(12) United States Patent
Adams

(10) Patent No.: US 6,268,478 B1
(45) Date of Patent: Jul. 31, 2001

(54) INTRACELLULAR VITAMIN D BINDING PROTEIN

(75) Inventor: John S. Adams, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 08/797,358

(22) Filed: Feb. 11, 1997

Related U.S. Application Data

(60) Provisional application No. 60/011,491, filed on Feb. 12, 1996.

(51) Int. Cl.[7] .............................. C07K 14/47; C07H 21/04

(52) U.S. Cl. .................... 530/350; 536/23.5; 530/358

(58) Field of Search .................................... 530/350, 358; 536/23.5

(56) References Cited

PUBLICATIONS

Gacad et al. Identification and Partial characterization of a Non–Receptor Competitive Binding Protein for 1,25 Dihydroxy–Vitamin $D_3$ in Vitamin D–Resistant New World Primate Cells. Clinical Research 40(2): 207A, 1st col. (Abstract) (1992).

Gacad et al. Specificity of Steroid Binding in New World Primate B95–8 Cells with a Vitamin D–Resistant Phenotype. Endocrinology 131(6): 2581–2587 (1992).

Arbelle et al. Specificity of Vitamin D Sterol Binding to the Vitamin D Resistance–Causing Intracellular Binding Protein in New World Primates. Clinical Research 41(2): 238A. 1st col. (Abstract) (1993).

Gacad et al. Purification of a Novel Vitamin D Binding Protein From Vitamin D–Resistant New World Primate Cells. Clinical Research 41(2): 153A, 2nd col. (Abstract) (1993).

Arbelle et al., "Structural determinants of ligand binding to the vitamin D resistance–causing intracellular vitamin D binding protein in new world primates", *J. Bone Min. Res.*, 8:S226 (1993).

Gacad and Adams, "Partial characterization of an intracellular non–receptor vitamin D binding protein in vitamin D–resistant new world primate cells", *J. Bone Min. Res.*, 7:151S (1992).

Gacad and Adams, "Identification of competitive binding component in vitamin D–resistant new world primate cells with a low affinity but high capacity for 1,25–dihydroxyvitamin $D_3$", *J. Bone Min. Res.*, 8:27–35 (1993).

Gacad and Adams, "The intracellular vitamin D binding protein (IDBP) in vitamin D–resistant new world cells in a member of the heat shock protein–70 (hsp–70) family", Abstract P3–725 *10th International Congress of Endocrinology*, p. 936 (1996).

(List continued on next page.)

*Primary Examiner*—Gary L. Kunz
*Assistant Examiner*—Eileen B. O'Hara
(74) *Attorney, Agent, or Firm*—Campbell & Flores LLP

(57) ABSTRACT

The invention relates to the discovery and purification of novel intracellular vitamin D binding proteins (IDBPs) and the isolation of polynucleotide sequences encoding the proteins. IDBPs are of interest because they mediate the vitamin D resistance, i.e., insensitivity, observed in new world primates. IDBPs are distinct from the vitamin D receptor and other intracellular receptors, e.g. estrogen receptor. One aspect of the invention is to provide purified IDBPs as pharmaceutical compositions to affect steroid hormone activity. Another aspect of the invention provides polynucleotides encoding the IDBPs of the invention for use in altering the expression of IDBPs. Yet another aspect of the invention is to provide assays for the detection or screening of therapeutic compounds that interfere with the interaction between IDBP and vitamin D (or other ligands that bind to IDBP), and the use of such compounds as pharmaceutical compositions.

27 Claims, 11 Drawing Sheets

OTHER PUBLICATIONS

Gacad and Adams, "The intracellular vitamin D binding protein overexpressed in vitamin D–resistant new world primate cells is a member of the heat shock–70 family of proteins", *J. Bone Min. Res.* 11:S162 (1996).

Gacad et al., "Purification and functional characterization of an intracellular vitamin D binding protein in vitamin D–resistant new world primate cells", Abstract OR12–1 *Endocrine Society 77th Annual Meeting* p. 61 (1995).

Wu et al., "Molecular cloning of a partial cDNA for the intra–cellular vitamin D binding protein from vitamin D–resistant new world primate cells: sequence similarity at the nucleotide level with the heat shock protein–70 family", *J. Bone Min. Res.*, 11:S318 (1996).

```
             50        60        70        80        90       99
Idbp    GCGGCGCCGTCCCGCTGAGTCAGCCCGGGAGGGCGGGAGGCTCTCTGCCGG-CCGGGAAA
                 |||||||| ||    |   ||  ||| ||
X51757      CCCGGGCGGGCGAGAGGCTCTCAACTGGGCGGGAAGGTGCGGGAAGGTGCGGAAAG
(HSP70B)         10        20        30        40        50

100       110       120       130       140       150      159
Idbp    GTGCGGGAANGTTCGCGGCGGCGCNGGCGGGAAGAAGCGCAANCGGATAAAAAGCCCGTG
        || ||  ||| :||||||||||||| :||  ||  || |||||| : |||||||||||||
X51757  GTTCGCGAAAGTTCGCGGCGGCGGGGGTCGGGTGAGGCGCAAAAGGATAAAAAGCCCGTG
             60        70        80        90       100       110

160       170       180       190       200       210
Idbp    GAAGCGAANCGCANTANATCCGARCCGGGCTGGCCGGAAACAAATCGCGGGGAGA--CCC
        ||||||  |:|   |: |:||||||:||||||||| |  | | ||| |||||  | |
X51757  GAAGCGGAGCTGAGCAGATCCGAGCCGGGCTGGCTGCAGAGACACCGCAGGGAGAGCCTC
             120       130       140       150       160       170

220       230       240       250       260       270
Idbp    ACGGCGGAGCGCCCTTCGACTGCTGATCGGCAGCAGCCTCAACGGCCTCGAGCATCC-AC
        || || |||||||| |||||  || || |||||||||||  |||||| ||||||||| ||
X51757  ACTGCTGAGCGCCCCTCGACGGCGGACGGGCAGCAGCCTCCGTGGCCTCCAGCATCCGAC
             180       190       200       210       220       230

START                  ─ATP B.
             280       290       300       310       320       330
Idbp    GAWAAGCTTCAGCC[ATG]CAGGCCCCACGGGAGCTGGCG[GTGGGCATCGA]CCTGGGCACCA
        |  |||||||||||  ||  |||||||||||||||||||||   ||||||||||||||||||||
X51757  AAGAAGCTTCAGCC ATG CAGGCCCCACGGGAGCTCGCG GTGGGCATCGA CCTGGGCACCA
             240       250       260       270       280       290

340       350       360       370       380       390
Idbp    CCTACTCGTGCGTGGGCGTGTTCACAACAGGGCCGCGTGGAGATCCTGGCCAACGAACNA
        ||||||||||||||||||||||  || |||||||||||||||||||||||||||||  ||:|
X51757  CCTACTCGTGCGTGGGCGTGTT-TCAGCAGGGCCGCGTGGAGATCCTGGCCAACG-ACCA
             300       310       320       330       340       350

400       410       420       430       440       450
Idbp    GGGCAACCGCACCAMGCCMATCTACGTKGCCCTTCACTGACACCAACCNGCTGGTCNGGA
        ||||||||||||||:|||:| |||||:|||||||||||:|||||||| | |:||||||:||||
X51757  GGGCAACCGCACCACGCCCAGCTACGTGGCCCTTCACCGACACCGAGCGGCTGGTCGGGA
             360       370       380       390       400       410
```

FIG.3A

```
            460        470        480        490        500        510
Idbp   CGCNGCCATCAACCAAGCGGSCCTGAACCCGCTCAACACGGTGTTCNACGCCAATCGGCG
       ||| :||||  | ||| |||||:|||||||||||| ||||||||||||||:| ||||| ||||
X51757 CGCCGGCCAAGAGCCAGGCGGCCCTGAACCCCCACAACACCGTGTTCGATGCCAAGCGGC-
            420        430        440        450        460        470

520        530        540        550        560        570
Idbp   GTGATCGGGCGCAAGTTCGCGGACGCCACGGTGCAGGCGGACATGAAGCACTGGCCCTTC
       |||||||||||||||||||||||| ||||||||||| ||||||||||||||||||||||||
X51757 -TGATCGGGCGCAAGTTCGCGGACACCACGGTGCAGTCGGACATGAAGCACTGGCCCTTC
             480        490        500        510        520        530

580        590        600        610        620        630
Idbp   CAGGTGGTGAGCGAGGGCTGCAAGCCCAAGGTGCGCGTGTCCTACCGCGGGGAGGACAAG
       | |||||||||||||||| |||||||||||||||| ||  || ||||||||||||||||||
X51757 CGGGTGGTGAGCGAGGGCGGCAAGCCCAAGGTGCCGGTATCGTACCGCGGGGAGGACAAG
             540        550        560        570        580        590

640        650        660        670        680        690
Idbp   TCGTTCTACCCCGAGGAGATCTCGTCCATGGTGCTGAGCAAGATGAAGGAGACGGCCGAG
       | |||||||||||||||||||||||||||||||||||||||||||||||||||||||||||
X51757 ACGTTCTACCCCGAGGAGATCTCGTCCATGGTGCTGAGCAAGATGAAGGAGACGGCCGAG
             600        610        620        630        640        650

700        710        720        730        740        750
Idbp   GCGTATCTGGGCCAGCCCGTGAAGCACGCTGTGATCACCGTGCCCGCCTACTTCAATGAC
       ||||| .|||||||||||||||||||||| |||||||||||||||||||| ||||||||||
X51757 GCGTACCTGGGCCAGCCCGTGAAGCACGCAGTGATCACCGTGCCCGCCTATTTCAATGAC
             660        670        680        690        700        710

760        770        780        790        800        810
Idbp   TCGCAGCGCCAGGCCACCAAGGACGCGGGCGCTATCGCGGGGCTCAACGTGCTGCGGATC
       |||||||||||||||||||||||||||||||| ||||||||||||||||||||| |||||||
X51757 TCGCAGCGCCAGGCCACCAAGGACGCGGGGGCCATCGCGGGGCTCAACGTGTTGCGGATC
             720        730        740        750        760        770

820        830        840        850        860        870
Idbp   ATCAACGAACCTACGGCTGCCGCCATCGCCCATGGGCTGGACCGGCGCGGCGCGGGAGAA
       ||||| || ||  ||||| || ||||||||| |||||||||||||||| |||||||||||||
X51757 ATCAATGAGCCCACGGCAGCTGCCATCGCCTATGGGCTGGACCGGCGGGGCGCGGGAGAG
             780        790        800        810        820        830
```

FIG.3B

```
         880       890       900       910       920       930
Idbp     CGCAACGTGCTCATTTTTGACCTGGGTGGGGGCACCTTCGACGTGTCCGTTCTCTCCATT
         ||||||||||||||||||||||||||||||||||||||||| ||||| ||||||||||||
X51757   CGCAACGTGCTCATTTTTGACCTGGGTGGGGGCACCTTCGATGTGTCGGTTCTCTCCATT
         840       850       860       870       880       890

940       950       960       970       980       990
Idbp     GACGCCGGTGTCTTTGAGGTGAAAGCCACTGCTGGAGACACCCACTTGGGTGGAGARGAC
         ||||| |||||||||||||||||||||||||||||||| |||||| ||||| |||||:|||
X51757   GACGCTGGTGTCTTTGAGGTGAAAGCCACTGCTGGAGATACCCACCTGGGAGGAGAGGAC
         900       910       920       930       940       950

1000      1010      1020      1030      1040      1050
Idbp     TTCGACAACCGGTTGGTGAACCACTTTGTGGAAGAATTCCGGCGGAAGCATCSGAAGGAC
         |||||||||||| | |||||||||| |||||||||||||||||||||||||:|||||||
X51757   TTCGACAACCGGCTCGTGAACCACTTCATGGAAGAATTCCGGCGGAAGCATGGGAAGGAC
         960       970       980       990       1000      1010

1060      1070      1080      1090      1100      1110
Idbp     CTGAGCTGGAACAAGANGGCCCTTCGCAGGCTGCCGCACAGCCTGTGAGCGCGCCAAGCGC
         |||||| ||||||||| : |||||  ||||||||||||||||||||||||||||||||||
X51757   CTGAGCGGGAACAAGCGTGCCCTCGGCAGGCTGCCGCACAGCCTGTGAGCGCGCCAAGCGC
         1020      1030      1040      1050      1060      1070

1120      1130      1140      1150      1160      1170
Idbp     ACCCTGTCCTCCAGCACCCAGGCCACCCTGGANATTGACTCCCTGTTCGARGGCGTGGAC
         ||||||||||||||||||||||||||||||||:|| |||||||||||||||:||||||||
X51757   ACCCTGTCCTCCAGCACCCAGGCCACCCTGGAGATAGACTCCCTGTTCGAGGGCGTGGAC
         1080      1090      1100      1110      1120      1130

1180      1190      1200      1210      1220      1230
Idbp     TTCTACACGTCCATCACTCGTGCCCGCTTTGANGAACTGTGCTCANACCTCTTCCGCANC
         ||||||||||||||||||||||||||||||||:|||||||||||||:|||||||||||:|
X51757   TTCTACACGTCCATCACTCGTGCCCGCTTTGAGGAACTGTGCTCAGACCTCTTCCGCAGC
         1140      1150      1160      1170      1180      1190

1240      1250      1260      1270      1280      1290
Idbp     ACTCTGGAACCGGTANAAAAAGSCCTGCGGGATGCCAANCTGGACAAGG-CCANATCCAT
         || ||||| ||||| :| || |:|||||||||||||||:||||||||||   |||:|| |||
X51757   ACCCTGGAGCCGGTGGAGAAGGCCCTGCGGGATGCCAAGCTGGACAAGGCCCAGATTCAT
         1200      1210      1220      1230      1240      1250
```

FIG.3C

```
       1300       1310       1320       1330       1340       1350
Idbp   GACCTCSTCCTGGGTGGGGGGCTCCACTCSCATCCCCARGGTACARAAGTTGCTGCAGGA
       ||||||:|||| ||||||||||||||||||:||||||||:||| ||:|||||||||||||
X51757 GACGTCGTCCT-GGTGGGGGGCTCCACTCGCATCCCCAAGGTGCAGAAGTTGCTGCAGGA
       1260       1270       1280       1290       1300       1310

1360       1370       1380       1390       1400       1410
Idbp   CTTCTTCMACGGCAAGGAGCTGAACAAGAGCATCAACCCTGATGAAGCTGTGGCCTATGG
       ||||||:|||||||||||||||||||||||||||||||||||||| |||||||||||||
X51757 CTTCTTCAACGGCAAGGAGCTGAACAAGAGCATCAACCCTGATGAGGCTGTGGCCTATGG
       1320       1330       1340       1350       1360       1370

ATP B. ←——|——→ SUBSTRATE B
       1420       1430       1440       1450      1460       1470
Idbp   GGCTGCGGTGCANGCGGCCGTGTTGATGGGGGACAAGTGTGAGAAAGTGCGGGATCTTCT
       |||||| |||||| ||||||||||||||||||||| ||||||||||||| |||| | ||
X51757 GGCTGCTGTGCAGGCGGCCGTGTTGATGGGGGACAAATGTGAGAAAGTGCAGGATCTCCT
       1380       1390       1400       1410       1420       1430

1480       1490       1500       1510       1520       1530
Idbp   GCTGCTGGATGTGGCTCCCCTGTCTCTAGGGCTGGAGACAGCAGGTGGGGTGATGACTAC
       |||||||||||||||||||||||||||| |||||||||||||||||||||||||| ||
X51757 GCTGCTGGATGTGGCTCCCCTGTCTCTGGGGCTGGAGACAGCAGGTGGGGTGATGACCAC
       1440       1450       1460       1470       1480       1490

1540       1550       1560       1570       1580       1590
Idbp   GCTTATCCAGAGGAATGCCACTATCCCCACCAAGCAGACCCAGACTTTCACCACCTACTC
       ||| |||||||||| |||||||||||||||||||||||||||||||||||||||||||||
X51757 GCTGATCCAGAGGAACGCCACTATCCCCACCAAGCAGACCCAGACTTTCACCACCTACTC
       1500       1510       1520       1530       1540       1550

1600       1610       1620       1630       1640       1650
Idbp   GGACAACCAGCCTGGGGTCTTCATCCANGTGTATGANGGTGAGAGGGCCATGACCAANGA
       ||||||||||||||||||||||||||| |||||||:||||||||||||||||||||:||
X51757 GGACAACCAGCCTGGGGTCTTCATCCAGGTGTATGAGGGTGAGAGGGCCATGACCAAGGA
       1560       1570       1580       1590       1600       1610

1660       1670       1680       1690       1700       1710
Idbp   CAACAACCTGCTGGGGCGCTTTGAACTCAGTGGCATCCCTCCTGCCCCACGTGGAGTCCC
       |||||||||||||||| ||||||||||||||||||||||||||||||||||||||||||
X51757 CAACAACCTGCTGGGGCGTTTTGAACTCAGTGGCATCCCTCCTGCCCCACGTGGAGTCCC
       1620       1630       1640       1650       1660       1670
```

FIG.3D

```
            1720      1730      1740      1750      1760      1770
Idbp   CCAGATANAAGTGACCTTTGACATTGATGCTAATGGCATCCTGAGTGTGACAGCCACTGA
       ||||||| :| |||||||||||||||||||||||||||||||||||| |||||||||||||
X51757 CCAGATAGAGGTGACCTTTGACATTGATGCTAATGGCATCCTGAGCGTGACAGCCACTGA
            1680      1690      1700      1710      1720      1730

1780      1790      1800      1810      1820      1830
Idbp   CAGGAGCACAGGTAAGGCTAACAAGATCACCATCACCAATGACAAGGGCCGGCTGAGCAA
       ||||||||||||||||||||||||||||||||||||||||||||||||||||||||||||
X51757 CAGGAGCACAGGTAAGGCTAACAAGATCACCATCACCAATGACAAGGGCCGGCTGAGCAA
            1740      1750      1760      1770      1780      1790

1840      1850      1860      1870      1880      1890
Idbp   GGAAGAGGTGGAGAGGATGGTTCGTGAGGCCGANCAATACAAAGCTGAGGATGAGGCCCA
       ||| ||||||||||||||||||| ||| ||||||: ||||| ||||||||||||||||||
X51757 GGAGGAGGTGGAGAGGATGGTTCATGAAGCCGAGCAGTACAAGGCTGAGGATGAGGCCCA
            1800      1810      1820      1830      1840      1850

SUBSTRATE B.    ←—|—→  OLIGOMERIZATION B.
            1900      1910      1920      1930|     1940      1950
Idbp   GAGGGACAGAGTGGCTGCCAAAAACTCGTTGGAGACCCATGTCTTCCATGTGAAAGGTTC
       |||||||||||||||||||||||||||||||| ||||| |||||||||||||||||||||
X51757 GAGGGACAGAGTGGCTGCCAAAAACTCGCTGGAGCCCATGTCTTCCATGTGAAAGGTTC
            1860      1870      1880      1890      1900      1910

1960      1970      1980      1990      2000      2010
Idbp   TTTGCAAGAGGAAAGCCTTAGGGACAAGATTCCCAAAGAGGACAGGCACAAAGTGCAAGA
       |||||||||||||||||||||||||||||||||||| ||||||||||| ||||  |||||
X51757 TTTGCAAGAGGAAAGCCTTAGGGACAAGATTCCCGAAGAGGACAGGCGCAAAATGCAAGA
            1920      1930      1940      1950      1960      1970

2020      2030      2040      2050      2060      2070
Idbp   CAAGTGTCAGGAAGTCCTTGCCTGGCTGGAGCACAACCAGCTGGCAGACAAGGAGGAGTA
       |||||||| |||||||||||||||||||||||||||||||||||||| ||||||||||||
X51757 CAAGTGTCGGGAAGTCCTTGCCTGGCTGGAGCACAACCAGCTGGCAGAGAAGGAGGAGTA
            1980      1990      2000      2010      2020      2030

2080      2090      2100      2110      2120      2130
Idbp   TGAGCATCAGAAGARGGAGCTGGAGCAAATCTGTCGCCCCATCTTCTCCAGGCTCTTAWG
       ||||||||||||| ||||||||||||||||||||||||||||||||||||||||| ||:|
X51757 TGAGCATCAGAAGAGGGAGCTGGAGCAAATCTGTCGCCCCATCTTCTCCAGGCTC-TATG
            2040      2050      2060      2070      2080      2090
```

FIG.3E

```
              2140      2150      2160      2170      2180      2190
Idbp   GGGGACCTKGTGTCCCTGGGGGCAGCAGTTGTGGCGYTCAAGCCCGCCAGGGGGACCGCA
       |||| |||:||||||||||||||||||||||||||| :|||||||||||||||| ||
X51757 GGGGGCCTGGTGTCCCTGGGGGCAGCAGTTGTGGCACTCAAGCCCGCCAGGGGGACCCCA
              2100      2110      2120      2130      2140      2150
                                        STOP
              2200      2210      2220   SIGN 2230      2240      2250
Idbp   GCACCGGCCCCATCATTGARGARGTTGATTGAATGGCCCTTTGTGATAAGTCAGCTGTGA
       ||||||||||||||||||||:||:||||||||||||||||| ||||||||||||||||||
X51757 GCACCGGCCCCATCATTGAGGAGGTTGATTGAATGGCCCTTCGTGATAAGTCAGCTGTGA
              2160      2170      2180      2190      2200      2210

2260      2270      2280      2290      2300      2310
Idbp   CTGTAAGGGCTATGCTGTKGGCCTTCTAGACTGT-TTCTATGATCCTGCCCTTCCGAGAT
       ||||  |||||||||||| :||||||||||||||| |||||||||||||||||| |||||
X51757 CTGTCAGGGCTATGCTATGGGCCTTCTAGACTGTCTTCTATGATCCTGCCCTTCAGAGAT
              2220      2230      2240      2250      2260      2270

2320      2330      2340      2350      2360      2370
Idbp   GAAGGGCTGGGGAATCTTCCCCGCAAAGCTAGAGCTTTCTTCTCAGGATGTTTCATAACT
       |||  ||   |||||    |||| |||||||| ||||||||| ||||||   |  | ||
X51757 GAA---CT--------TTCCCTCCAAAGCTAGAACTTTCTTCCCAGGATAACTGAAGTCT
                        2280      2290      2300      2310

2380      2390      2400      2410      2420      2430
Idbp   GAAGTCTTTTGACTTTTCGGTGAGAGAGAGGTTCATCCTCTTCTGCTTCAAATTAAAAGT
         | |||||  |||||||| ||||||||||||||||||||||||||||||||
X51757 TTTGACTTTTTGCGGGGAGGGCGGTTCATCCTCTTCTGCTTCAAATAAAAAGTCATTAAT
              2320      2330      2340      2350      2360      2370
```

FIG. 3F

```
1    MQAPRELAVG  IDLGTTYSCV  GVFQQGRVEI  LANDQGNRTT  PIYVAFTDTN

51   RLVGDAAINQ  AALNPLNTVF  DANRLIGRKF  ADATVQADMK  HWPFQVVSEG

101  CKPKVRVSYR  GEDKSFYPEE  ISSMVLSKMK  ETAEAYLGQP  VKHAVITVPA

151  YFNDSQRQAT  KDAGAIVGLN  VLRIINEPTA  AAIAHGLDRR  GAGERNVLIF

201  DLGGGTFDVS  VLSIDAGVFE  VKATAGDTHL  GGEDFDNRLV  NHFVEEFRRK

251  HRKDLSWNKR  ALRRLRTACE  RAKRTLSSST  QATLEIDSLF  EGVDFYTSIT

301  RARFEELCSD  LFRSTLEPVE  KGLRDAKLDK  AXIHDVVLVG  GSTRIPRVQK

351  LLQDFFNGKE  LNKSINPDEA  VAYGAAVQAA  VLMGDKCEKV  RDLLLLDVAP

401  LSLGLETAGG  VMTTLIQRNA  TIPTKQTQTF  TTYSDNQPGV  FIQVYEGERA

451  MTKDNNLLGR  FELSGIPPAP  RGVPQIEVTF  DIDANGILSV  TATDRSTGKA

501  NKITITNDKG  RLSKEEVERM  VREAEQYKAE  DEAQRDRVAA  KNSLETHVFH

551  VKGSLQEESL  RDKIPKEDRH  KVQDKCQEVL  AWLEHNQLAD  KEEYEHQKRE

601  LEQICRPIFS  RLYGGPGVPG  GSSCGAQARQ  GDRSTGPIIE  EVD
```

FIG.4

INTRACELLULAR VITAMIN D BINDING PROTEIN

RELATED APPLICATION DATA

This application is a continuation-in-part of U.S. Provisional Application No. 60/011,491, filed Feb. 12, 1996.

This invention was made in part with support from the National Institutes of Health (NIH). The United States government may have certain rights to the invention.

FIELD OF THE INVENTION

The invention is in the field of vitamin D and steroid hormone signaling.

BACKGROUND

Most genera of new world primates exhibit vitamin D resistance. This resistance is biochemically characterized by the maintenance of a high circulating concentration of the active vitamin D hormone 1,25 dihydroxyvitamin D(1,25-(OH)2D) and the prohormone 25-hydroxyvitamin D(25-OHD). Clinical manifestations of vitamin D resistance include rickets in rapidly growing adolescent animals deprived of adequate sunlight exposure. Old world primates, including humans, do not exhibit vitamin D resistance. Levels of 25-OHD may be as much as ten fold lower, and levels of 1,25-(OH)$_2$D as much as 100 fold lower, in old world primates than those observed in most new world primates. Vitamin D resistance phenomenon in new world primates also correlates with high circulating levels of other steroid hormones including glucocorticoid (Chrousos et al. *Endocrinology* 115:25–32 (1984), Lipsett et al. *Recent Prog. Hormone Res.* 42:199–246 (1985), Brandon et al. *Cancer Res.* 49:2203–2213 (1989)), mineral corticoid, progesterone, testosterone, 17β-estradiol (Chrousos et al. *J. Clin. Endocrinol. Metab.* 58:516–920 (1984)), 1,25-(OH)$_2$D (Takahashi et al. *Biochem S.* 227:555–563 (1985)).

Unlike the majority of resistant states described for other steroid hormones and vitamin D in humans, resistance to vitamin D in new world primates does not appear to be related to a mutation in the vitamin D receptor (VDR) protein. Rather, the vitamin D resistant state in new world primates is associated with the apparent high expression of an intracellular vitamin D binding protein (IDBP). IDBP is distinct from members of the serum vitamin D binding protein/albumin families of proteins in that IDBP is cysteine poor. Additionally, while serum vitamin D binding protein/albumin and vitamin D/steroid receptor protein families are principally confined to the extracellular domain and nucleus of the cell, respectively, IDBP predominantly localizes in the cell cytoplasm. However, like these other sterol/steroid binding proteins, IDBP preferentially binds 25-hydroxylated vitamin D metabolites.

IDBP activity has been enriched from extracts of new world primate cells. Nevertheless, numerous attempts to purify IDBP to homogeneity were unsuccessful. Therefore, the precise biochemical characteristics and primary molecular structure of IDBP remained elusive.

By gaining an understanding of the biochemical mechanisms behind vitamin D resistance and the high levels of circulating steroid hormones in new world primates, new opportunities for treating and diagnosing diseases related to either over-production or under-production of vitamin D and other steroidal hormones may be achieved. Such diseases include osteoporosis, hypercalcemia, and vitamin D intoxications.

SUMMARY OF THE INVENTION

The invention relates to the discovery and purification of novel intracellular vitamin D binding proteins (hereinafter "IDBP") and the isolation of polynucleotide sequences encoding the proteins. Surprising, these IDBPs are heat shock proteins. The human homolog of IDBP is more commonly known as the heat shock protein hsp70. However, the property of steroid hormone binding has not been previously recognized in heat shock proteins. IDBPs are of interest because they mediate the vitamin D resistance, i.e., insensitivity, observed in new world primates. IDBPs are distinct from the vitamin D receptor and other intracellular receptors such as the estrogen receptor. IDBPs can interfere with the biological activity of the vitamin D receptor and other related intracellular receptor proteins. IDBPs of the invention can competitively bind to a variety of steroid compounds that normally bind to intracellular receptor proteins. These steroids include vitamin D, 17β-estradiol, testosterone, and progesterone. By binding to such steroid compounds, IDBPs may both prevent the ligands from interacting with their cognate intracellular receptor and serve to concentrate the intracellular receptors. Thus by regulating the intracellular levels of the subject IDBPs, desirable physiological effects may be obtained. Such effects may be used to treat a variety of diseases involving signaling at intracellular receptors including osteoporosis, glucocorticoid mediated disorders, and hypercalcemia associated with vitamin D overproduction, granuloma forming diseases.

One aspect of the invention is to provide compositions of purified IDBPs for use as mediators of steroid compound activity. The purified proteins may be obtained from either recombinant cells or naturally occurring cells. The purified intracellular vitamin D binding proteins of the invention may be mammalian in origin. Primate, including human and *Callithrix jacchus* (common marmoset), derived IDBPs are examples of the various IDBPs specifically provided for. The invention also provides allelic variants and biologically active derivatives of naturally occurring IDBPs.

Another aspect of the invention is to provide polynucleotides encoding the IDBPs of the invention and to provide polynucleotides complementary to the polynucleotide coding strand. The polynucleotides of the invention may be used to provide for the recombinant expression of IDBPs. The polynucleotides of the invention may also be used for genetic therapy purposes so as to treat diseases related to intracellular receptors that bind ligands that bind to IDBPs. The invention also provides polynucleotides for use as hybridization probes and amplification primers for the detection of naturally occurring polynucleotides encoding IDBPS. Preferred polynucleotides are those which encode the *Callithrix jacchus*-derived IDBP.

Another aspect of the invention is to provide antibodies capable of binding to the IDBPs of the invention for use in altering steroid compound activity. The antibodies may be polyclonal or monoclonal. The invention also provides methods of using the subject antibodies to detect and measure expression of vitamin D binding protein either in vitro or in vivo.

Another aspect of the invention is to provide assays for the detection or screening of therapeutic compounds that interfere with the interaction between IDBP and vitamin D (or other ligands that bind to IDBP). The assays of the invention comprise the step of measuring the effect of a compound of interest on binding between IDBP and vitamin (or other ligands that bind to IDBP). Binding may be measured in a variety of ways, including the use of labeled IDBP or labeled ligands.

BRIEF DESCRIPTION OF THE DRAWINGS

FIG. 1A shows the ability of various metabolites at 100 nM to compete with 4 nM of [$^3$H] 25-hydroxyvitamin D3 for binding to IDBP. FIG. 1B illustrates the displacement of 4 nM of [$^3$H] 25-hydroxyvitamin D3 through increasing concentrations of competitive 25-hydroxylated vitamin D metabolites.

FIGS. 3A–F is an alignment of the cDNA for *Callithrix jacchus* IDBP (SEQ ID NO: 1) on the upper line, with that of human inducible heat shock protein (hsp70) (SEQ ID NO: 2) on the lower line.

FIG. 4 is the deduced sequence Idhp.pep generated symbols 1 to 643.

DESCRIPTION OF THE SPECIFIC EMBODIMENTS

Figure 1A:
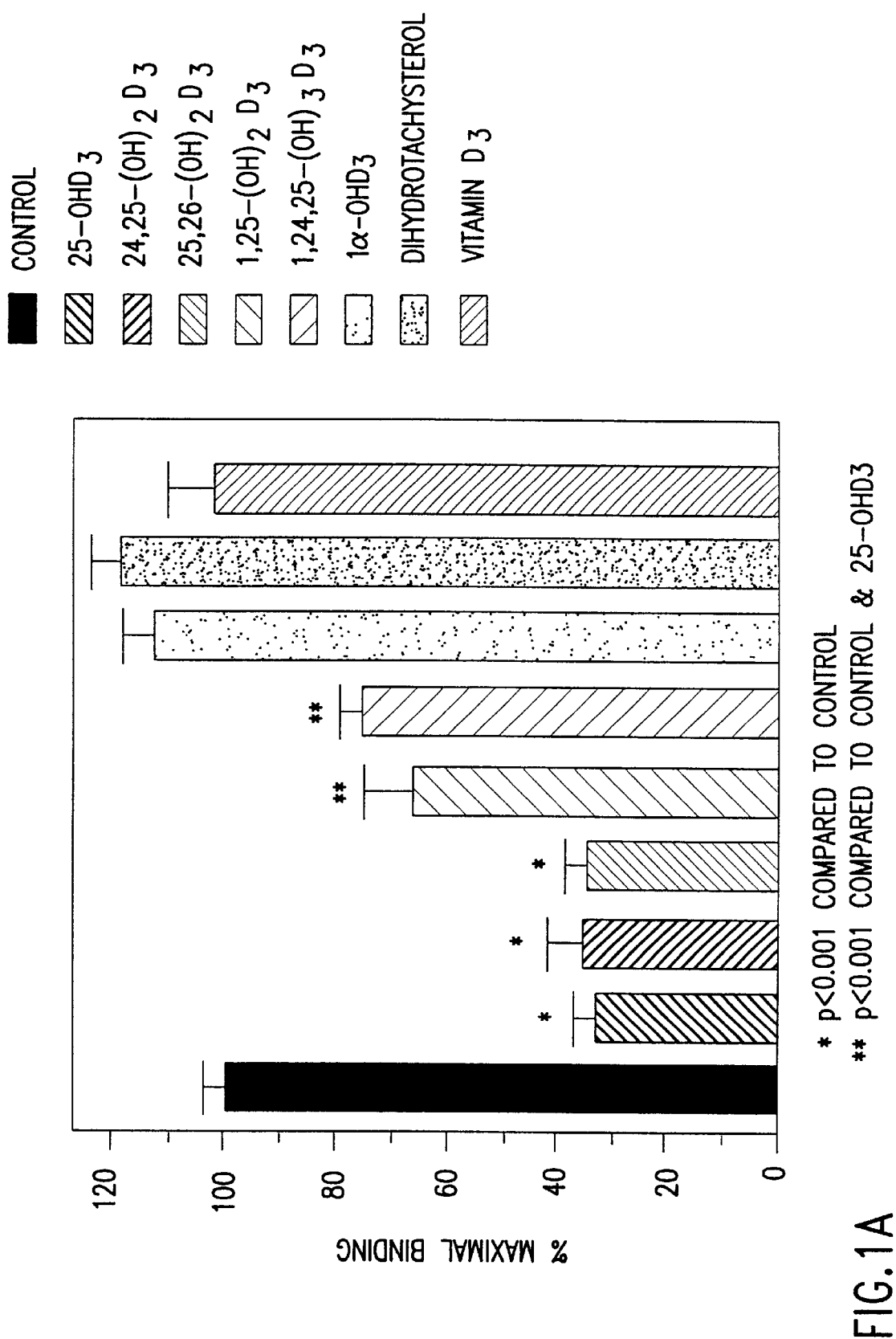
FIGS. 1A and 1B present experimental data relating to the competitive displacement of [$^3$H] 25-hydroxyvitamin D3 from IDBP by vitamin D3 sterols.

The term "vitamin D" is used broadly herein. Unless noted otherwise, the term "vitamin D" includes both the natural mammal-derived form of vitamin D (vitamin D3, cholecalciferol), the plant-derived form of vitamin D (vitamin D2, ergocalciferol) and various metabolites of vitamin D such as 25-hydroxy vitamin D (25 [OH] D), 1,25 dihydroxy vitamin D (1,25 [OH]$_2$D), 25,26-dihydroxy vitamin D (25,26 [OH]$_2$D), and the like.

The vitamin D intracellular binding proteins for use in the methods of the invention have the biological activity of binding to 25-hydroxy vitamin D2 (vitamin D2), 25-hydroxy vitamin D3 (vitamin D3), or one or more similar compounds as noted in Table I that has a relative binding index (RBI) greater than 0. The IDBPs of the invention may be isolated from a variety of mammalian animal species. Preferred mammalian species for isolation are primates, including humans. New world primates are particularly preferred for isolation of IDBP. Although humans and old world primates do not produce large enough quantities of IDBP to manifest the vitamin D resistance phenomenon seen in new world primates, humans and old world primates (as well as other mammals) do produce IDBPS. For example, the human hsp70 protein is a functional IDBP.

The invention also contemplates allelic variants of IDBP for use in the methods of the invention. IDBPs may be prepared from a variety of mammalian tissues; however, leukocytes and cell lines established from blood leukocytes are preferred non-recombinant sources of IDBPs. IDBPs may be isolated from non-recombinant cells in a variety of ways well known to a person of ordinary skill in the art. One example of such an isolation method is provided below in the Examples section.

IDBPs may also be obtained from recombinant host cells genetically engineered to express significant quantities of IDBPs. Methods for purifying recombinant proteins from genetically engineered host cells vary with the host cell type and are well known to persons of ordinary skill in the art. Such IDBPs may be administered to subjects in order to decrease the biological activity of steroid hormones, as described below.

The invention also provides, in one of its aspects, the polynucleotide and amino acid sequence of *Callithrix jacchus* IDBP. Experiments with this IDBP indicated that the amino terminus of the protein is blocked. The amino acid residue sequence of the individual internal tryptic digest fragments IDBP isolated from *Callithrix jacchus* leukocytes suggested that this protein is a member of the heat shock family of proteins. The polynucleotide sequence of a cDNA encoding the IDBP of *Callithrix jacchus* and the deduced amino acid residue sequence are provided in FIGS. 3 and 4, respectively. The IDBP of *Callithrix jacchus* has a relative molecular weight of about 60–65 kDa (kilodaltons), as determined by SDS-PAGE.

The term "intracellular vitamin D binding protein" or "IDBP" as used herein refers not only to proteins having the amino acid residue sequence of naturally occurring IDBPs (such as human hsp70 protein) but also refers to functional derivatives and variants of naturally occurring IDBP. A functional derivative of a native IDBP is a compound that has a qualitative biological activity in common with a native IDBP, e.g., binding to vitamin D3 and other cognate ligands. "Functional derivatives" include, but are not limited to, fragments of native polypeptides from any animal species (including humans), and derivatives of native (human and non-human) polypeptides and their fragments, provided that they have a biological activity in common with a respective native polypeptide. "Fragments" comprise regions within the sequence of a mature native polypeptide. For example, as shown below by way of example, a portion of IDBP which includes the deduced ATP binding domain of IDBP from about amino acid residues 8 to 388 of SEQ ID NO:3, is a fragment which binds vitamin D and related steroid molecules. Other deduced fragments of IDBP are the substrate binding domain from about amino acid residues 389 to 547 of SEQ ID NO:3, and the variable domain from about amino acid residues 548 to 643 of SEQ ID NO:3.

The term "derivative" is used to define amino acid sequence and glycosylation variants, and covalent modifications of a native polypeptide, whereas the term "variant" refers to amino acid sequence and glycosylation variants within this definition. Preferably, the functional derivatives are polypeptides which have at least about 65% amino acid sequence identity, more preferably about 75% amino acid sequence identity, even more preferably at least 85% amino acid sequence identity, most preferably at least about 95% amino acid sequence identity with the sequence of a corresponding native polypeptide. Most preferably, the functional derivatives of a native IDBP retain or mimic the region or regions within the native polypeptide sequence that directly participate in ligand binding. The phrase "functional derivative" specifically includes peptides and small organic molecules having a qualitative biological activity in common with a native IDBP.

Amino acid sequence variants of native IDBPs and IDBP fragments are prepared by methods known in the art by introducing appropriate nucleotide changes into a native or variant IDBP encoding DNA, or by in vitro synthesis of the desired polypeptide. Targeted or random mutations may be introduced using a variety of techniques well known in the art such as site specific mutagenesis and PCR mutagenesis. Details of the foregoing and similar mutagenesis techniques are found in general textbooks, such as, for example, Sambrook et al., *Molecular Cloning: H Laboratory Manual 2nd edition,* Cold Spring Harbor Press, Cold Spring Harbor (1989), and *Current Protocols in Molecular Biology,* Ausubel et al. eds., John Wiley and Sons (1995).

Since it is often difficult to predict in advance the characteristics of a variant IDBP, it will be appreciated that screening will be needed to select the optimum variant. For this purpose biochemical screening assays, such as those described hereinbelow, are provided.

Polynucleotides for use in the Methods of the Invention

The invention also provides for isolated polynucleotides that encode IDBPs. The polynucleotides may encode complete IDBPs or portions thereof. The polynucleotides may be produced by a variety of methods including in vitro chemical synthesis using well known solid phase synthesis technique, by cloning or combinations thereof. The polynucleotides may be single stranded or double stranded. Polynucleotide complementary to polynucleotides encoding IDBPs are also provided. The polynucleotides may be derived from cDNA or genomic libraries. Persons of ordinary skill in the art are familiar with the degeneracy of the genetic code and may readily design polynucleotides encoding IDBPs that have either partial or complete polynucleotide sequence homology to naturally occurring polynucleotide sequences encoding IDBPs. The polynucleotides useful in the invention include not only the polynucleotides of the invention derived from *Callithrix jacchus,* but also polynucleotides encoding other IDBPs, such as human hsp70s.

Polynucleotides may be used as hybridization probes to recover IDBPs from genetic libraries. The polynucleotides may also be used as primers for the amplification of IDBP encoding polynucleotides or a portion thereof through the polymerase chain reaction (PCR) and other similar amplification procedures. The polynucleotides may also be used as probes and amplification primers to detect mutations in IDBP encoding genes that have been correlated with diseases, particularly diseases related to overexpression or underexpression of ligands for IDBP.

The invention also provides a variety of polynucleotide expression vectors comprising the IDBPs of the invention, as well as other IDBPs. Expression vectors comprise a polynucleotide sequence encoding an IDBP in functional combination with one or more promoter sequences so as to provide for the expression of the IDBP (or an anti-sense copy of the sequence suitable for inhibition of expression of an endogenous gene). The vectors may comprise additional polynucleotide sequences for gene expression, regulation, or the convenient manipulation of the vector, such as terminators, enhancers, selective markers, packaging sites, and the like. Detailed description of polynucleotide expression vectors and their use can be found in, among other places *Gene Expression Technology: Methods in Enzymology* Volume 185 Goeddel ed, Academic Press Inc., San Diego, Calif. (1991), *Protein Expression in Animal Cells* Roth ed., Academic Press, San Diego, Calif. (1994).

The polynucleotide expression vectors have a variety of uses. Such uses include the genetic engineering of host cells to express IDBPs. The polynucleotide expression vectors may also be used for genetic therapy for diseases and conditions in which it may be desirable use to express IDBPs at levels greater than naturally occurring expression levels. Alternatively, it may be desirable to use the vectors of the invention for anti-sense expression to reduce the naturally occurring levels of IDBP.

The invention encompasses methods for the treatment of a variety of diseases characterized by undesirably high levels of vitamin D or other steroids that can bind to IDBPs of the invention. Diseases may be treated through either in vivo or in vitro genetic therapy. Protocols for genetic therapy through the use of viral vectors can be found, among other places, in *Viral Vector Gene Therapy and Neuroscience Applications,* Kaplit and Lowry, Academic Press, San Diego (1995). The genetic therapy methods of the invention comprise the step of introducing a vector for the expression of IDBP (or inhibitory anti-sense RNA) into a patient cell. The patient cell may be either in the patient, i.e., in vivo genetic therapy, or external to the patient and subsequently reintroduced into the patient, i.e., in vitro genetic therapy. Diseases that may be treated by the subject genetic therapy methods include osteoporosis, renal bone disease, vitamin D toxicity, glucocorticoid hormone overproduction, sex steroid hormone overexpression and underexpression, hypercalcemia (attributable to vitamin D overexpression), estrogen responsive breast and ovarian cancer, testosterone responsive prostrate cancer, and the like.

Screening Assays for Compounds which Alter IDBP Activity

Another aspect of the invention is to provide assays useful for determining if a compound of interest can bind to IDBPs so as to interfere with the binding of vitamin D (or other ligands) to the intracellular vitamin receptor protein. The following assays are designed to identify compounds that interact with (e.g., bind to) IDBP, compounds that interact with (e.g., bind to) intracellular proteins that interact with IDBP, compounds that interfere with the interaction of IDBP with steroid hormones, and to compounds which modulate the activity of the IDBP gene (i.e., modulate the level of IDBP gene expression) or modulate the level of IDBP. Assays may additionally be utilized which identify compounds which bind to IDBP gene regulatory sequences (e.g., promoter sequences) and which may modulate IDBP gene expression. See e.g., Platt, K. A., 1994, J. Biol. Chem. 269:28558–28562, which is incorporated herein by reference in its entirety.

The compounds which may be screened in accordance with the invention include but are not limited to peptides, antibodies and fragments thereof, prostaglandins, lipids and other organic compounds (e.g., terpines, peptidomimetics) that bind to IDBP and either mimic the activity triggered by the natural ligand (i.e., agonists) or inhibit the activity triggered by the natural ligand (i.e., antagonists); as well as peptides, antibodies or fragments thereof, and other organic compounds that mimic the IDBP natural ligand.

Such compounds may include, but are not limited to, peptides such as, for example, soluble peptides, including but not limited to members of random peptide libraries (see, e.g., Lam, K. S. et al., 1991, Nature 354:82–84; Houghten, R. et al., 1991, Nature 354:84–86), and combinatorial chemistry-derived molecular library peptides made of D- and/or L-configuration amino acids, phosphopeptides (including, but not limited to members of random or partially degenerate, directed phosphopeptide libraries; see, e.g., Songyang, Z. et al., 1993, Cell 72:767–778); antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof); and small organic or inorganic molecules.

Other compounds which can be screened in accordance with the invention include but are not limited to small organic molecules that are able to gain entry into an appropriate cell and affect the expression of the IDBP gene (e.g., by interacting with the regulatory region or transcription factors involved in gene expression); or such compounds that affect the activity of IDBP (e.g., by inhibiting or enhancing the binding of IDBP to steroid hormone).

Computer modelling and searching technologies permit identification of compounds, or the improvement of already identified compounds, that can modulate IDBP expression or activity. Having identified such a compound or composition, the active sites or regions are identified. Such active sites might typically be the binding partner sites, such as, for example, the interaction domains of the IDBP protein with its cognate ligand. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential IDBP modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of IDBP protein interactions, and related transduction factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in treating conditions associated with the under or over production of steroid hormones. Assays for testing the effectiveness of compounds are discussed below.

In vitro systems may be designed to identify compounds capable of interacting with (e.g., binding to) IDBP. Compounds identified may be useful, for example, in modulating the activity of wild type and/or mutant IDBP gene products. In vitro systems may be utilized in screens for identifying compounds that disrupt normal IDBP interactions.

The principle of the assays used to identify compounds that bind to the IDBP involves preparing a reaction mixture of the IDBP protein and the test compound under conditions and for a time sufficient to allow the two components to interact and bind, thus forming a complex which can be removed and/or detected in the reaction mixture. The IDBP species used can vary depending upon the goal of the screening assay. For example, where agonists of the natural ligand are sought, the full length IDBP, or a fusion protein containing IDBP fused to a protein or polypeptide that affords advantages in the assay system (e.g., labeling, isolation of the resulting complex, etc.) can be utilized.

The screening assays can be conducted in a variety of ways. For example, one method to conduct such an assay would involve anchoring the IDBP protein, polypeptide, peptide or fusion protein or the test substance onto a solid phase and detecting IDBP/test compound complexes anchored on the solid phase at the end of the reaction. In one embodiment of such a method, the IDBP reactant may be anchored onto a solid surface, and the test compound, which is not anchored, may be labeled, either directly or indirectly. In another embodiment of the method, an IDBP protein anchored on the solid phase is complexed with labeled antibody. Then, a test compound could be assayed for its ability to disrupt the association of the IDBP/antibody complex.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for IDBP protein, polypeptide, peptide or fusion protein, or the test compound to anchor any complexes formed in solution, and a labeled antibody specific for the other component of the possible complex to detect anchored complexes.

The macromolecules that interact with the IDBP protein are referred to, for purposes of this discussion, as "binding partners". The binding partners of interest here are the steroid hormones which bind to IDBP. Therefore, it is desirable to identify compounds that interfere with or disrupt the interaction of such binding partners with IDBP which may be useful in regulating the activity of IDBP and thus the response to steroid hormones.

The basic principle of the assay systems used to identify compounds that interfere with the interaction between the IDBP protein and its binding partner or partners involves preparing a reaction mixture containing IDBP protein, polypeptide, peptide or fusion protein as described above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the IDBP moiety and its binding partner. Control reaction mixtures are incubated without the test compound or with a placebo. The formation of any complexes between the IDBP moiety and the binding partner is then detected. The formation of a complex in the control reaction, but not in the reaction mixture containing the test compound, indicates that the compound interferes with the interaction of IDBP and the interactive binding partner.

The assay for compounds that interfere with the interaction of IDBP and binding partners can be conducted in a heterogeneous or homogeneous format. Heterogeneous assays involve anchoring either IDBP moiety product or the binding partner onto a solid phase and detecting complexes anchored on the solid phase at the end of the reaction. In homogeneous assays, the entire reaction is carried out in a liquid phase. The examples below describe similar assays which may be easily modified to screen for compounds which disrupt or enhance the interaction. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with IDBP moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either IDBP moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the IDBP gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of IDBP moiety and the interactive binding partner is prepared in which either IDBP or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt IDBP/intracellular binding partner interaction can be identified.

In a particular embodiment, an IDBP fusion can be prepared for immobilization. For example, IDBP or a peptide fragment, e.g., corresponding to the ATP binding domain, can be fused to a glutathione-S-transferase (GST) gene using a fusion vector, such as pGEX-5X-1, in such a manner that its binding activity is maintained in the resulting fusion protein. The interactive binding partner can be labeled with radioactive isotope, for example, by methods routinely practiced in the art. In a heterogeneous assay, e.g., the GST-IDBP fusion protein can be anchored to glutathione-agarose beads. The interactive binding partner can then be added in the presence or absence of the test compound in a manner that allows interaction and binding to occur. At the end of the reaction period, unbound material can be washed away. The interaction between the IDBP gene product and the labeled interactive binding partner can be detected by measuring the amount of radioactivity that remains associated with the glutathione-agarose beads. A successful inhibition of the interaction by the test compound will result in a decrease in measured radioactivity.

Alternatively, the GST-IDBP fusion protein and the labeled interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of IDBP/binding partner interaction can be detected by measuring the radioactivity associated with the beads.

In another embodiment of the invention, these same techniques can be employed using peptide fragments that correspond to the binding domains of IDBP, in place of the full length proteins. Any number of methods routinely practiced in the art can be used to identify and isolate the binding sites. These methods include, but are not limited to, mutagenesis of the gene encoding the protein and screening for disruption of binding in a co-immunoprecipitation assay. Sequence analysis of the gene encoding the protein will reveal the mutations that correspond to the region of the protein involved in interactive binding.

Assays for Identification of Compounds that Ameliorate Disorders Involving IDBPs Compounds, including but not limited to binding compounds identified via assay techniques such as those described above, can be tested for the ability to ameliorate conditions associated with over-production of steroids, particularly those steroids identified in Table I by an RBI of greater than 0, by activating IDBP protein. Additionally, compounds which interfere with the activity of IDBP protein may be used to treat conditions where there is insufficient steroid hormone, such as in menopause or any number of demineralization diseases. The assays described above can identify compounds which affect IDBP activity (e.g., compounds that bind to IDBP, inhibit binding of the natural ligands, or activate binding of the natural ligands, and compounds that bind to a natural ligand of IDBP and neutralize the ligand activity); or compounds that affect IDBP gene activity (by affecting IDBP gene expression, including molecules, e.g., proteins or small organic molecules, that affect or interfere with splicing events so that expression of the full length form of IDBP can be modulated). Such compounds can be used as part of a therapeutic method for the treatment of steroid hormone activity disorders, and for treatment of conditions associated with steroid hormone activity.

The invention encompasses cell-based and animal model-based assays for the identification of compounds exhibiting such an ability to ameliorate steroid hormone activation disorder symptoms. Such cell-based assay systems can also be used as the standard to assay for purity and potency of the compounds, including recombinantly or synthetically produced IDBP mutants.

Cell-based systems can be used to identify compounds which may act to ameliorate steroid hormone activation disorder symptoms. Such cell systems can include, for example, recombinant or non-recombinant cells, such as cell lines, which express the IDBP gene. For example leukocyte cells, or cell lines derived from leukocyte cells can be used. In addition, expression host cells (e.g., B95 cells, COS cells, CHO cells, OMK cells, fibroblasts, Sf9 cells) genetically engineered to express a functional IDBP and to respond to activation by the natural ligand, as measured by a chemical or phenotypic change (e.g., binding of vitamin D or other steroid, etc.), or induction of another host cell gene such as a steroid responsive gene, can be used as an end point in the assay.

In utilizing such cell systems, cells may be exposed to a compound suspected of exhibiting an ability to affect IDBP activity or activation, at a sufficient concentration and for a time sufficient to elicit such an effect in the exposed cells. After exposure, the cells can be assayed to measure alterations in the expression of the IDBP gene, e.g., by assaying cell lysates for IDBP mRNA transcripts (e.g., by Northern analysis) or for IDBP protein expressed in the cell; compounds which regulate or modulate expression of the IDBP gene are valuable candidates as therapeutics. Alternatively, the cells are examined to determine whether one or more IDBP/steroid cellular phenotypes has been altered to resemble a more normal or more wild type phenotype, or a phenotype more likely to produce a lower incidence or response to steroid. For example, the activation of vitamin D responsive genes may be assayed.

In addition, animal-based steroid hormone disorder systems, which may include, for example, mice, may be used to identify compounds capable of affecting steroid activation or repression disorder-like symptoms. For example, there are a number of model systems which comprise "knockdown" mice expressing reduced levels of steroid hormone or steroid hormone receptor. A mouse with reduced levels of the thyroid hormone receptor exhibits hormone resistance. In addition, there are a number of mouse models of targeted overexpression of receptors which would serve as steroid-responsive models. Such animal models may be used as test systems for the identification of drugs, pharmaceuticals, therapies and interventions which may be effective in treating such disorders.

As an example, animal models may be exposed to a compound suspected of exhibiting an ability to interfere with the binding of IDBP to steroid hormone such as vitamin D, at a sufficient concentration and for a time sufficient to elicit an amelioration of symptoms of insufficient vitamin D in the exposed animals. The response of the animals to the exposure may be monitored by assessing the reversal of disorders associated with a vitamin D deficiency such as rickets. With regard to intervention, any treatments which reverse any aspect of steroid hormone over or under production disorder-like symptoms should be considered as candidates for human disorder therapeutic intervention. Dosages of test agents may be determined by deriving dose-response curves, as discussed below.

Antibodies for use in the Methods of the Invention

Antibodies to IDBPs may also be used in the methods of the invention, both diagnostically and therapeutically. Polyclonal antibodies to IDBPs generally are raised in animals by multiple subcutaneous (sc) or intraperitoneal (ip) injections of an IDBP and an adjuvant. Suitable animals include any non-human mammals such as rabbits, mice, goats, sheep, horse, rats. Alternatively, for the generation of antibodies against proteins conserved in mammals, birds (such as chickens or turkeys), fish, and reptiles may be used to generate antibodies. It may be useful to conjugate the an IDBP or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine resides), glutaraldehyde, succinic anhydride, $SOCl_2$, or $R_1N=C=NR$, where R and $R_1$ are different alkyl groups. Also, aggregating agents such alum are used to enhance the immune response.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, the anti-IDBP monoclonal antibodies of the invention may be made using the hybridoma method first described by Kohler & Milstein, Nature 256:495 (1975), or may be made by recombinant DNA methods (Cabilly, et al, U.S. Pat. No. 4,816,567).

The anti-IDBP specific antibodies have a number of uses in the methods of the invention. The antibodies may be used to purify IDBPs from either recombinant or non-recombinant cells. The subject antibodies may be used to detect and/or quantify the presence of IDBPs in tissue samples, e.g., from blood, skin, and the like. Quantitative of IDBPs may be used diagnostically for those diseases and physiological or genetic conditions that have been correlated with particular levels of IDBP expression levels.

Pharmaceutical Preparations and Administration

IDBPs, polynucleotides encoding IDBPs, and the compounds that are determined to affect IDBP gene expression or activity, or the interaction of IDBP with sterols, can be administered to a patient at therapeutically effective doses to treat or ameliorate diseases related to over or under production of vitamin D and other steroidal hormones. Such diseases include osteoporosis, hypercalcemia, vitamin D intoxications, menopause, estrogen receptor-positive breast or ovarian cancer, testosterone responsive prostate cancer, renal bone disease and vitamin D deficiency. Altered activity or expression of IDBPs may be used to maximize skeletal mineralization in adolescents and counter age-related demineralization. IDBP and IDBP stimulating compounds may also be used prophylactically, for example, as birth control reagents in both men and woman, to reduce the biological activity of steroid hormones. A therapeutically effective dose refers to that amount of the compound sufficient to result in amelioration of symptoms of steroid hormone over production or insufficiency.

When compounds identified in screening assays are to be delivered to a subject, toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention having been described above, may be better understood by referring to the following examples. The following examples are offered for the purpose of illustrating the invention and should not be interpreted as a limitation of the invention.

EXAMPLE I

Ligand Specificity of IDBP

In this experiment, we analyzed the ability of vitamin D3 and various of its metabolites to competitively displace [$^3$H]25-hydroxy vitamin D3 from unfractionated 100,000×g supernatant extracts to B95-8 cells. Additionally, we also tested the binding potential to IDBP of a number of non-vitamin D steroids and bioactive lipids.

Materials and Methods

Vitamin D Sterols, Steroids, and Other Compounds

[$^3$H]25-hydroxy vitamin D3 ([$^3$H]25-OHD3; specific activity 181 Ci/mmol) and [$^3$H]17β-estradiol were purchased from Amersham Corporation (Arlington Heights, Ill.). The source of other compounds evaluated as potential ligands is provided in Table I; three vitamin D analogues and RU486 were provided as gifts. All other buffer constituents were from Sigma Company (St. Louis, Mo.). The source and name of chromatographic supports used in protein purification are as follows: phenyl sepharose (low-sub, mid-sub and high-sub), butyl sepharose, octyl sepharose, and Mono-Q were from Pharmacia; BPS-DE and BPS-CM were from MetaChem; DEAE-5PW was from Millipore; and both BioRad Q and hydroxyapatite were from BioRad.

Culture and Extraction of B95-8 Cells. The B-lymphoblastoid cell line B95-8 was obtained from the American Type Culture Collection (ATCC, Manassas, Va.). This cell line was established by EBV transformation of blood leukocytes from the vitamin D-resistant new world primate, *Callithrix jacchus* (common marmoset). The cell line was maintained in RPMI-1640 medium (Irvine Scientific, Irvine, Calif.) routinely supplemented with 10% fetal calf serum (FCS; Gemini BioProducts, Calabasas, Calif.), 100 units/ml penicillin, 100 μg/ml streptomycin, 2 mM L-glutamine (both from Gibco-BRL, Grand Island, N.Y.) in an atmosphere of 95% air-5% $CO_2$.

Confluent cultures were harvested by agitation to dislodge clumps of lymphoblasts that were weakly adherent to the plastic flask. Harvested cells were pelleted and washed twice in ice cold phosphate-buffered saline (PBS; 20 mM $Na_2HPO_4$ and 150 mM NaCl, pH 7.2). The pelleted cells were then resuspended in ETD buffer (1 mM EDTA, 10 mM Tris-HCl, 5 mM dithiothreitol, pH 7.4) containing 1 mM phenylmethylsulfonylflouride and homogenized by Polytron on ice in five 15-second bursts. Nuclei with associated nuclear steroid receptor proteins, were pelleted at 4,000×g for 30 minutes at 4° C. The post-nuclear supernatant of this spin was then subjected to high-speed centrifugation at 100,000×g for 1 hour at 4° C. The resulting "100,000×g supernatant" was either aliquoted and stored at 70° C. for further study, used in competitive ligand binding analyses, or subjected to further purification as described below in Example II.

Ligand Binding Analyses. The ability of the unfractionated 100,000×g supernatant extracts of B95-8 cells and individual column fractions of chromatographically-purified material to bind [$^3$H]25-OHD3 in the presence or absence of increasing concentrations of radioinert compounds (see Table I) was performed by competitive protein binding assay as previously described in Gacad et al. *Bone Min. Res.* 8:27–35 (1993). Unfractionated extract as well as post-anion exchange and post-hydrophobic interaction chromatography fractions were adjusted with ETD buffer (pH 8.0) to contain a NaCl concentration of 0.5 M prior to assay; specific binding of [$^3$H]25-OHD3 to IDBP(s) was found to be equivalent or superior to specific binding in the traditional assay buffer of KETD (ETD containing 0.3M KCl, pH 7.4).

Briefly, unfractionated or post-FPLC fractions were incubated in ETD-0.5 M NaCl overnight at 4° C. with 4 nM [3H]25-OHD3 in the presence or absence of 1–100 nM unlabeled competitive ligand. Protein-bound [$^3$H]25-OHD3 was separated from unbound sterol by incubation with dextran-coated charcoal. Specifically-bound 25-OHD3 was determined by subtracting the mean of duplicate determinations of binding in the presence of 100 nM radioinert competitive ligand from the mean of determinations of binding in the absence of added competitive ligand. Specific binding of 17β-[$^3$H]estradiol as well as [$^3$H]25-OHD3 to IDBP(s) was also determined in individual fractions eluting from hydroxyapatite chromatography. The binding assay conditions were the same as those stated above except that specific binding was determined in ETD-0.3 M $Na_2HPO_4$ buffer (pH 6.8).

Statistical Analysis. Experimental values for sterol/steroid binding under varying conditions were compared using Student's t test for unpaired samples.

Results

Binding of Vitamin D Metabolites and Analogs. The ability of vitamin D3 and various of its metabolites to competitively displace [$^3$H]25-OHD3 in unfractionated 100,000×g supernatant extracts of B95-8 cells is shown in FIG. 1. When incubated with extract at a 100 nM concentration, the naturally occurring metabolites 25-OHD3, 24,25-(OH)$_2$D3 and 25,26-(OH)$_2$D3 were roughly equivalent in their ability to competitively inhibit 2 nM of [$^3$H]25-OHD3 binding. Polarization of the competitive ligand by addition of a C-1 alpha-hydroxyl, the only naturally occurring site of metabolic hydroxylation in the A-ring of vitamin D3, to 1,25-(OH)$_2$D$_3$ and 1,24,25-(OH)$_3$D3 significantly decreased effective competitive binding. Two synthetic compounds which possess a C-1 alpha-hydroxyl group (1-OHD3 or a pseudo C-1 alpha-hydroxyl group (dihydrotachysterol) but which lack hydroxyl substitutions in the molecular side chain were also incapable of displacing [$^3$H]25-OHD3. Vitamin D3 which is not modified in the side chain and lacks a C-1 alpha-hydroxyl was similarly ineffective as a competitive ligand at a 100 nM concentration.

Figure 1B:
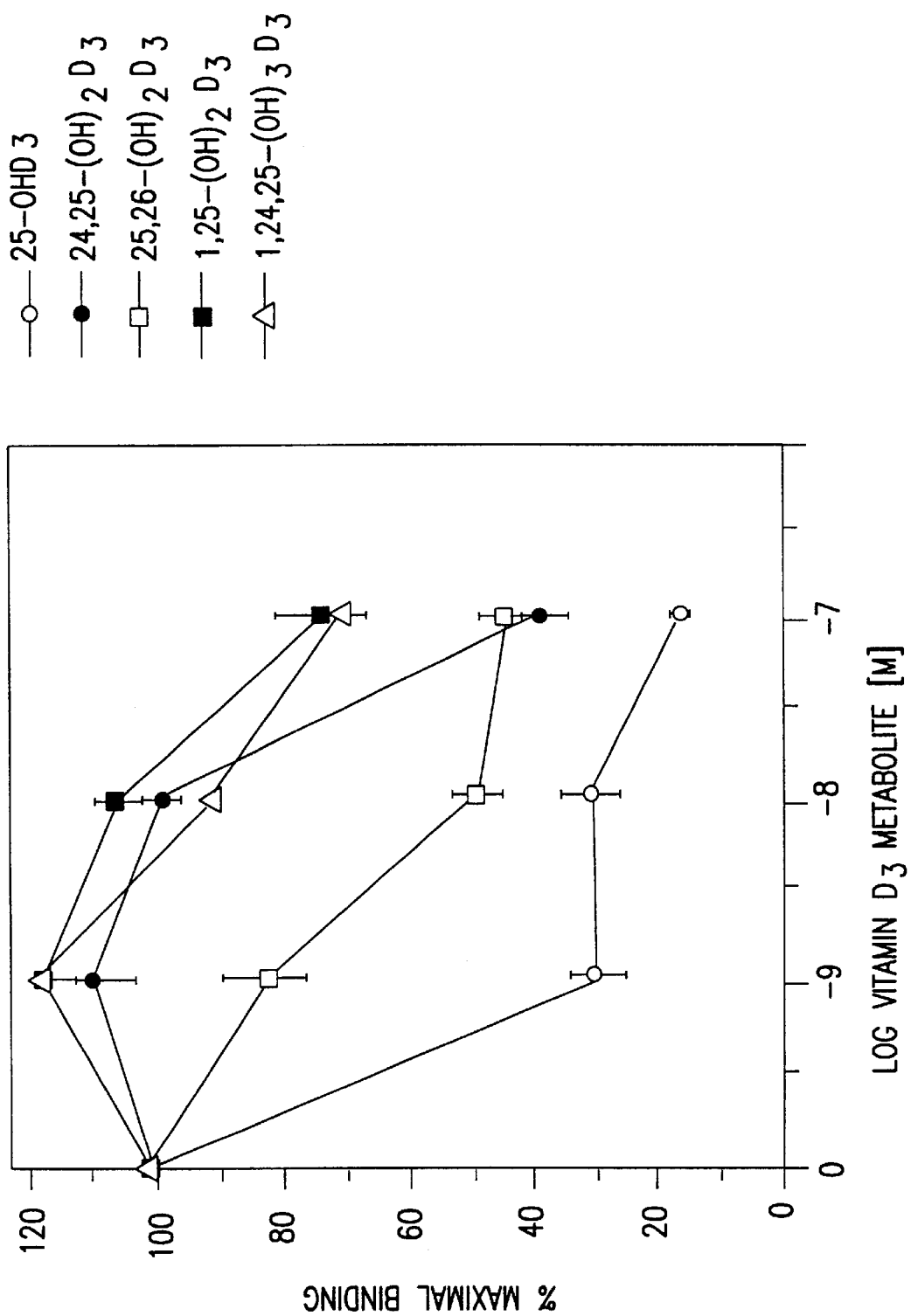
Figure 2A:
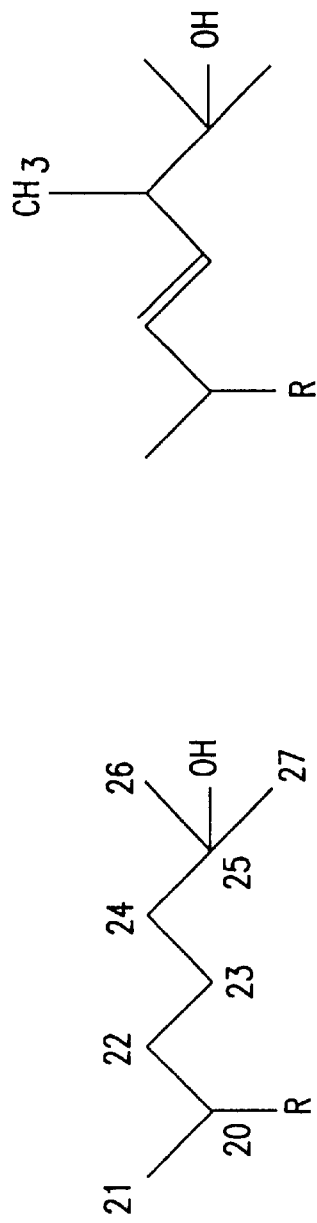
FIG. 2A diagrams the structure of naturally occurring 1,25-dihydroxyvitamin D3 and 1,25-dihydroxyvitamin D2, as well as three synthetic analogs; the vitamin D2 metabolites are characterized by the presence of a C-24 methyl group and a C-22-23 double bond, while the nonhypercalcemia-causing vitamin D analogs all have structural alterations in the terminal aspect of the sidechain.
Figure 2A:
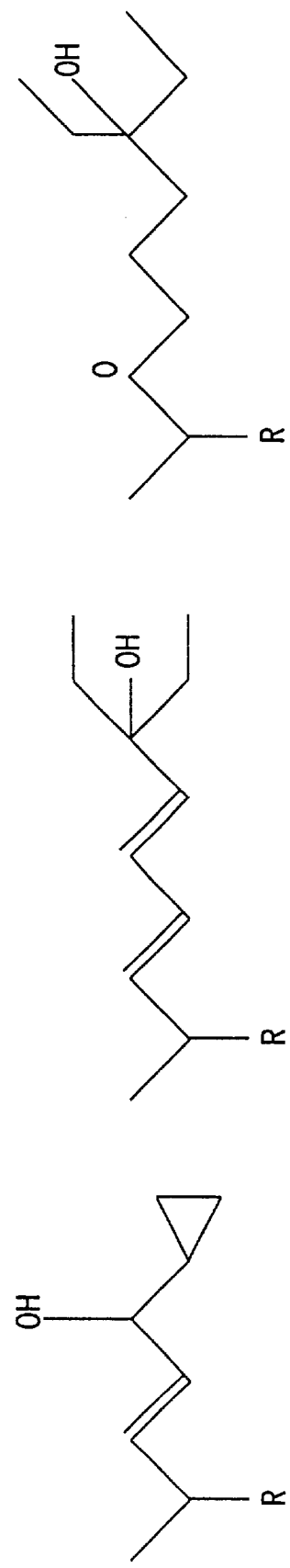
Figure 2B:
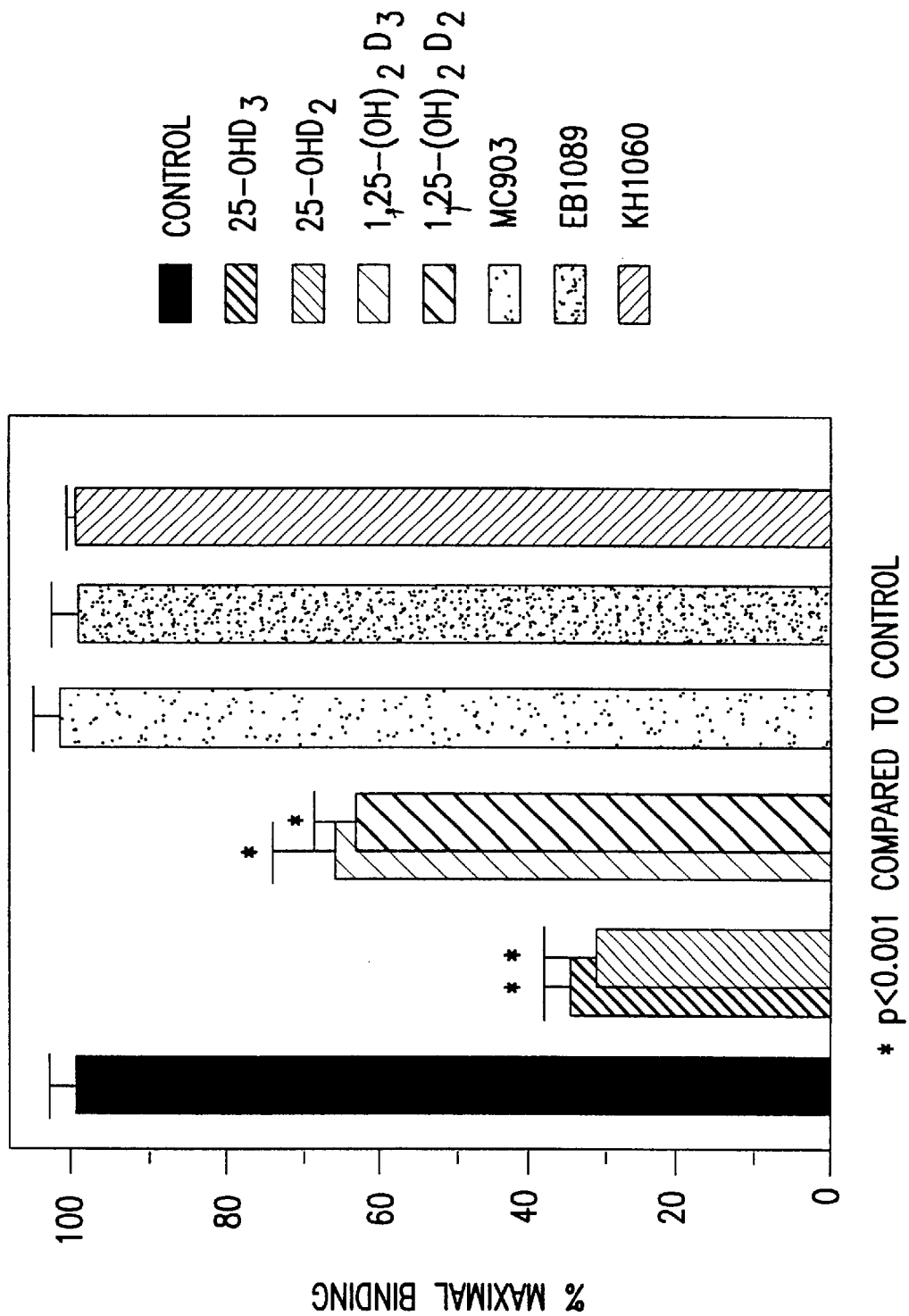
FIG. 2B is a graph of experiments measuring the binding of vitamin D3, D2 and other related compounds to IDBP. Data are expressed as the percent maximal binding of 4 nM [$^3$H] 25-hydroxyvitamin D3 in the absence of added competitor; each data point is the mean±SD of at least three replicates.

[$^3$H]25-OHD3 displacement by serial dilution of those vitamin D3 metabolites shown to be effective competitive inhibitors of [$_3$H]25-OHD3 binding is shown in FIG. 1B. Assuming an 80% displacement of bound [$^3$H]25-OHD3 as the maximal inhibition of binding, the ED$_{50}$ for binding could be determined for only three of the five metabolites: 25-OHD3; 25,26-(OH)$_2$D3 and 24,25-(OH)$_2$D3. 1,25-(OH)$_2$D3 and 1,24,25-(OH)$_2$-D3 displaced 25 OHD3 by only 20% at 10$^{-7}$M with no apparent displacement at lower concentrations. The ED$_{50}$ for 25-OHD3, 25,26-(OH)$_2$D3 and 24,25-(OH)$_2$D3 was 5×10$^{-10}$, 5×10$^{-9}$, and 5×10$^{-8}$M, respectively. Vitamin D2, a $\Delta_{5,7}$-diene steroid synthesized primarily in plants, differs structurally from vitamin D3 in the side-chain (FIG. 2A). Vitamin D2 and its metabolites possess a $\Delta_{22}$(C-22-C-23 double bond) and a C-24 methyl group which vitamin D3 and its metabolites do not. 25-OHD2 and 1,25-(OH)$^2$D2 were bound in unfractionated extracts equivalently to 25-OHD3 and 1,25-(OH)$^2$D3 (FIG. 2B). In contrast to modifications in the proximal portion of the side chain that do not alter sterol binding, structural changes in the terminal portion of the side chain that do not involve the hydroxylation of C-25 definitely do alter IDBP binding; for example, none of the C-1-hydroxylated nonhypercalcemic analogues MC903, EB1089 and KH1060 (FIG. 2A) were able to displace [$^3$H]25-OHD3 binding in unfractionated B95-8 extracts (FIG. 2B).

Binding of Non-Vitamin D Steroids and Bioactive Lipids. As depicted in Table I we also assessed the binding potential of a number of steroid precursor molecules, naturally occurring steroids, and two clinically useful steroid analogs, tamoxifen and RU486. With the exception of progesterone, 17β-estradiol, and testosterone, which competitively displaces [$^3$H]25-OHD3 in crude post-nuclear extracts of B95-8 cells, none of these evaluated compounds were able to compete with 25-OHD3 for binding in 100,000×g supernatant extracts of B95-8 cells. This includes 25-hydroxycholesterol, a molecule which bears the C-3 and C-25-hydroxyl groups but lacks the $\Delta_{5,7}$-diene structure of the preferred binder, 25-OHD3. Interestingly, none of the six steroid precursor molecules, glucocorticoids, mineralocorticoids, or the major intracellular metabolite of testosterone, 5-dihydrotestosterone, were capable ligands. The same lack of binding capacity was demonstrated with bioactive lipids in the arachidonic acid cascade as well as lipid molecules which bind to other members of the steroid receptor superfamily of proteins.

EXAMPLE II

Purification of IDBP

In an attempt to elucidate the nature of the IDBP protein, we subjected B95-8 cell extracts to a process of serial enrichment by physical and chemical means.

Materials and Methods

Chromatographic Separation and Enrichment of a [$^3$H] 25-OHD3 Binding Factor(s) in B95-8 Cell Extracts. The 100,000×g supernatant of the B95-8 cell extract was used in either competitive ligand binding analyses (see above) or as substrate for chromatographic enrichment of [$^3$H]25-OHD3 binding activity. Prior to a decision on the most effective supports for serial chromatographic purification of IDBPs, B95-8 100,000×g supernatant was subjected to chromatography over 11 different resins-five each for anion exchange and hydrophobic interaction chromatography and one for hydroxyapatite chromatography. Separation by ion exchange chromatography was examined through an inclining NaCl gradient using resins with different functional groups. Separation of proteins on the basis of their hydrophobicity through a declining NaCl gradient was examined over three different phenyl sepharose resins as well as over a butyl and octyl sepharose resin. Finally, chromatographic enrichment of [$^3$H]25-OHD3 ($^3$H labelled 25 hydroxy vitamin D) binding activity was analyzed over a hydroxyapatite support through a declining Na$_2$HPO$_4$ gradient. Each of these supports was evaluated for overall recovery of protein loaded onto the column as well as for enrichment in specific [$^3$H]25-OHD3 binding activity at pHs ranging from 6.8–8.0. Protein was assayed according to the method of Bradford.

On the basis of protein recovery, enrichment of bioactivity, ease of use, and resin available for FPLC and/or HPLC applications, three chromatographic supports, one each from the three different kinds of packing materials evaluated, were selected for serial chromatographic purification of IDBP(s): BPS-DE cellulose for anion exchange chromatography, phenyl sepharose (mid sub) for hydrophobic interaction chromatography, and HTP-hydroxyapatite for separation of proteins by their surface charge. The 100,000×g supernatant obtained from the extraction of ~10$^9$ B95-8 cells and solubilized in ETD buffer was diluted 1:1 with ETD (pH 8.0) buffer containing 0.1 M NaCl. The extract was then pumped onto a BPS-DE column equilibrated in ETD-0.1 M NaCl, using a Pharmacia FPLC system (Uppsala, Sweden). Elution of adsorbed proteins was accomplished with a linear NaCl-containing gradient ranging from 0.1–2.0 M NaCl at a flow rate of 1.0 ml/minute. Fractions containing protein with specific [$^3$H]25-OHD3 binding activity (eluting between 0.7–1.0 M NaCl) were collected and pooled. The anion exchange eluent of interest was adjusted to 2.5 M NaCl and applied to an FPLC column containing phenyl sepharose equilibrated in ETD-2.5 M NaCl (pH 8.0). Chromatography was achieved through a declining NaCl gradient (2.5–0 M) at a uniform flow rate. The majority of specific [$^3$H]25-OHD3 binding activity was recovered in the void volume and early gradient fractions. The eluent of interest from hydrophobic interaction chromatography was subjected to desalting and microconcentration over an Amicon membrane (nominal molecular weight cutoff of 3000 daltons) prior to reconstitution in ETD containing 0.01M Na$_2$HPO$_4$ (pH 6.8) and loading onto an HTP-hydroxyapatite FPLC column equilibrated in the same running buffer. Elution of [$^3$H]25-OHD3 binding proteins was achieved through a linear gradient of 0.01–0.4 M ETD-Na$_2$HPO$_4$ at a flow rate of 1.0 ml/minute.

Gel Filtration HPLC and SDS-Polyacrylamide Gel Electrophoresis (SDS-PAGE). Confirmation of the approximate molecular mass of 25-OHD3 moieties eluting from hydroxyapatite chromatography was sought by size exclusion HPLC (Waters/Millipore Corp., Milford, Mass.) over a column under non-denaturing conditions; an aliquot of two pooled fractions with [$^3$H]25-OHD3 binding activity from hydroxyapatite chromatography was injected and eluted in ETDA 0.3 M Na$_2$HPO$_4$ at a flow rate of 0.5 ml/minute. Individual 1.0 ml fractions were collected for reanalysis of specific 25-OHD3 binding potential. Another aliquot from these post-hydroxyapatite fractions was also subjected to PAGE under denaturing conditions.

Results

Purification of an IDBP (IBDP) Physicochemical Measures.

Under "low salt" extraction conditions, when the unoccupied vitamin D receptor was associated with the nuclear subfraction of the aqueous cell extract, IDBP was concentrated in the post-nuclear 4,000×g supernatant of the cell extract. Compared to 25-OHD3 uptake by whole cells, this partitioning lead to a 3.4-fold increase in specific [$^3$H]25-OHD3 binding (Table II). While the post 4,000×g supernatant of this material contained a relatively high content of total [$^3$H]25-OHD3 binding activity, it also contained a substantial quantity of non-specific binding, thus lowering the specific binding of [$^3$H]25-OHD3. In initial experiments aimed at IDBP purification this element of nonspecific sterol binding resulted in a relatively low rate of recovery of specific binding protein activity from subsequent column chromatography. Simply subjecting the 4,000×g postnuclear supernatant to ultracentrifugation (Table II) resulted in an additional 53% increase in specific binding; no specific [$^3$H]25-OHD3 binding was associated with the pellet of this high speed clarification of the post nuclear supernatant. Clarification of the postnuclear supernatant generally increased overall total protein recovery by 15–20% in subsequent column chromatographic purification of B95-8 cell extracts, presumably by removing lipid present in the "low-speed" 4,000×g post-nuclear extract of these cells.

Chromatographic Measures. The next step in IDBP purification was identification of useful chromatographic supports. Using the unfractionated 100,000×g supernatant of B95-8 cell extract as starting material, we evaluated the enrichment of [$^3$H]25-OHD3 binding activity after elution from three different kinds of supports containing resins for anion exchange, hydrophobic interaction, and hydroxylapatite chromatography. Based on the relative stability and capacity of unfractionated 100,000×g supernatant extract to bind [$^3$H]25-OHD3 at pH 8.0 (data not shown) anion exchange resins were initially chosen for separation of molecules on the basis of their net charge. Anion exchange chromatography was performed with chloride as the counterion over four different supports from five different vendors; in all cases the extract was loaded in NaCl and eluted through a 0.1–2.0 M NaCl gradient. With two "strong" anion exchange resins [$^3$H]25-OHD3 binding activity was not recovered in the elute. In contrast, elution of IDBP(s) from two "weak" anion exchange resins was achieved with a NaCl at a suitable concentration; enrichment of specific binding activity was 268-fold and 64-fold, respectively, for the BPS-DE and DEAE-5PW supports.

Hydrophobic interaction chromatography was also used to enrich specific [$^3$H]25-OHD3 binding in the 100,000×g supernatant extract of B95-8 cells. Presumably by virtue of their relatively modest degree of hydrophobicity, all of the phenyl-substituted resins examined provided much better recovery of specific binding activity than did either the butyl- or octyl-substituted resins. These results suggest that there was at least some degree of surface hydrophobicity to the IDBP(s) under nondenaturing conditions. Elution of specific [$^3$H]25-OHD3 binding activity from the phenyl-substituted resins was none-the-less achieved under high ionic strength buffer conditions in the absence of added detergent. A substantial increase in specific [$^3$H]25-OHD3 binding activity (and a coincident decrease in nonspecific binding) over the phenyl sepharose supports, despite the lack of apparent chromatography through a declining salt gradient, further suggested that this support was retaining more hydrophobic molecules that somehow interfered with sterol binding to IDBP(s).

Hydroxyapatite chromatography was also examined as a means of enriching the specific [$^3$H]25-OHD3 binding activity in 100,000×g supernatants of the NWP (new world primate) cell line. IDBP(s) was clearly absorbed to the BioRad hydroxyapatite resin in a low salt (phosphate) buffer and half of the loaded protein as well as a substantial amount of [$^3$H]25-OHD3 binding activity was recovered from the resin by elution through a Na$_2$PO$_4$ gradient (pH 6.8). These data suggest that when equilibrated in a phosphate buffer the IDBPs contain exposed amino groups (basic amino acids) which interact with the negatively charged groups in the hydroxyapatite matrix. Elution from the matrix at a relatively high phosphate concentration in the mobile phase supports the electrostatic interaction profile of a basic protein.

Serial Chromatograph of IDBP(s). Based on the above described findings with anion exchange chromatography over a BPS-DE cellulose support, hydrophobic interaction chromatography over a phenyl sepharose support, and hydroxyapatite chromatography independently and quantitatively enhance specific [$^3$H]25-OHD3 binding activity in extracts of the B95-8 cell line from a vitamin D resistant (New World Primate), we employed these same chromatographic steps in serial fashion to purify IDBP(s). The cumulative enrichment of specific [$^3$H]25-OHD3 binding activity through chromatography is depicted in the right panel of Table II.

Using the 100,000×g supernatant extract of B95-8 cells as starting material, anion exchange FPLC resulted in a substantial and predictable increase in specific [$^3$H]25-OHD3 binding activity that eluted from the column as a single, broad peak between 0.7–1.0 in the NaCl gradient. Fractions constituting this peak of sterol binding activity were pooled and applied to a phenyl sepharose FPLC column in a high ionic strength and eluted through a declining NaCl gradient. Elution of IDBP(s) with specific [$^3$H]25-OHD3 binding activity from this column was evident in the void volume of the column and complete before the salt concentration in the eluting gradient reached 2.0 M.

Although there was only a four-fold enrichment in specific binding activity over that achieved with anion exchange chromatography (Table II), hydrophobic interaction chromatography was important in separating the homodimer of glyceraldehyde-3-phosphate dehydrogenase (GAPDH) from IDBP(s); prior to institution of hydrophobic interaction chromatography in our serial purification scheme of IDBP (s), all attempts to acquire amino-terminal and internal amino acid sequence from proteins in the 60–65 kDa range excised from transblots of non-reducing 1% SDS-polyacrylamide gels resulted in identification of this co-migrating "housekeeping" gene product. Chromatographic separation of GAPDH and other proteins from IDBP(s) on the basis of their hydrophobicity dramatically improved the efficacy of hydroxyapatite chromatography in enrichment of proteins with specific [$^3$H]25-OHD3 binding activity (Table II). In the absence of preparative ion exchange and hydrophobic interaction chromatography, chromatography of 100,000×g supernatant extracts over a hydroxyapatite support resulted in a nearly 50-fold increase in [$^3$H]25-OHD3 binding activity. However, purification of IDBP(s) by charge and hydrophobicity prior to hydroxyapatite chromatography amplified the enrichment capability of hydroxyapatite FPLC more than 500% (50-fold vs 279-fold) for the protein(s) of interest.

There were two major peaks of specific [$^3$H]25-OHD3 binding activity in the eluent from hydroxyapatite chromatography, one eluting at 5.0 mM (peak I) and a smaller peak eluting at 100 mM (peak II) in the Na$_2$HPO$_4$ gradient. Specific sterol binding was noted at no other position in the gradient. To assess the apparent molecular mass of these binding moieties, an aliquot from the pooled fractions constituting peak I and peak II was subjected to gel filtration HPLC under nondenaturing conditions. Both peaks from hydroxyapatite chromatography exhibited specific [$^3$H]25-OHD3 binding activity in the range of 60–65 kDa; this was confirmed by "in gel" labeling with [$^3$H]25-OHD3. An aliquot of the hydroxyapatite eluate from peak I and peak II was also subjected to SDS-PAGE. Electrophoresis of the proteins in peak I and peak II revealed the presence of a doublet on the silver-stained gel with an apparent molecular mass of 60 and 62 kDa. These data suggested that one or both of these proteins was responsible for binding 25-OHD3.

Considering that sex steroids were also bound in post-nuclear as well as in 100,000×g supernatants of the post-nuclear nuclear extract of B95-8 cells, we examined the possibility that one or both of the 25-OHD3-binding peaks from hydroxyapatite chromatography was also responsible for gonadal steroid binding observed in the unfractionated extracts of B95-8 cells. Aliquots, matched for protein concentration, from post-hydroxyapatite peak I and peak II were incubated with tracer quantities of [$^3$H]25-OHD3 and [$^3$H]17β-estradiol in the presence and absence of 100 nM radioinert 25-OHD3 and 17β-estradiol. These studies disclosed that specific binding activity for 25-OHD3 exceeded by approximately 2-fold that of 17β-estradiol in both peak I and peak II and that there was no difference if the steroid/sterol binding profile between peak I and peak II, indicating that both hydroxyapatite fractions harbored both 25-OHD3 and 17β-estradiol binding capacity.

EXAMPLE III
Amino Acid Sequencing of IDBP

Serial chromatograph of B95-8 cellular extracts led to a dramatic enrichment of specific [$^3$H]25-OHD3 binding activity in purified extracts and led us to believe that a 60–65 kDa protein in our purified extracts was responsible for sterol binding.

Materials and Methods

Gel Electrophoresis and Amino Acid Sequencing. Post-hydroxyapatite fractions enriched for specific binding of 25-OHD3 were desalted, microconcentrated, and electrophoresed through an 11% discontinuous SDS-PAGE gel as described by Laemmli for one hour at 200 volts. Visualization of resolved proteins was accomplished with silver staining. The molecular weight of 25-OHD3-binding proteins was also estimated by specific "in-gel" binding of radiolabeled [$^3$H]25-OHD3. Following electrophoresis lanes of the gel were individually sliced, washed fine time, each for five minutes, in ETD buffer at 4° C., and then placed in a hybridization bag with 2.4 nM [$^3$H]25-OHD3 in ETD-0.5 M NaCl buffer in the presence or absence of 100 nM 25-OHD3. After overnight incubation at 4° C. on a rocker platform, the gels were washed several times in '25-OHD3 takedown buffer' containing 123 mM sodium barbital, 123 mM sodium acetate (pH 8.6), and 1 mM sodium azide without dextran or charcoal. The gel lanes were treated with Fluoro-Hance (RPI, Mt. Prospect, Ill.), dried under vacuum at 60° C. for one hour, and cut horizontally into 5 mm slices. Each gel slice was placed into scintillation vials containing Cytoscint (ICN, Irvine, Calif.) and radioactivity measured.

Aliquots of post-hydroxyapatite retentates were also subjected to two-dimensional electrophoresis as described by O'Farrell. Aliquots were loaded onto a pre-cast, pH gradient (pH 3–10) slab gel (Novex, San Diego, Calif.) and electrophoresed for one hour at 100 volts, a second hour at 200 volts, and finally at 500 volts for thirty minutes, separating proteins on the basis of their isolectric point. The lane containing the resolved proteins was fused onto an 8.5% SDS-PAGE preparative gel and electrophoresed for 80 minutes at 200 volts. Resolved proteins were either transblotted onto PVDF (CBB R250, BioRad, Hercules, Calif.) or subjected to 'in-gel' protease digestion prior to amino acid sequence analysis of the peptides. With respect to the former, the PVDF membrane was rinsed in distilled water three times for five minutes each. The membrane was stained for five minutes in 0.025% Coomassi Blue R-250 in 40:60 methanol:water, destained for fifteen minutes in 50% methanol, and allowed to dry at 23° C. The bands of interest were excised from the membrane and the protein extracted for analysis of amino acid composition, including cysteine content, prior to amino acid sequencing. Because the amino-terminus of the dominant protein of interest was blocked, generation of a panel of internal peptides was achieved by incubating coomassie stained gel slices with 1.0 μg trypsin/50 μg protein in 200 mM NH4HCO3 buffer. After overnight incubation at 37° C., the enzymatic reaction was neutralized and peptides extracted from the gel with the addition of 60% acetonitrile in 0.1% TFA. Extracted peptides or peptide fragments were purified by reverse phase HPLC on a C18 silica column (21 mm×250 mm, Vydac, Hesperia, Calif.) through a linear 0–80% acetonitrile gradient with an initial running condition of 100% 10 mM TFA. Peptides were resolved over a two hour period at a flow rate of 0.2 ml/min. Tryptic masses were screened for purity and integrity by matrix assisted laser desorption/ionization mass spectrometry (MALDI-MS). Selected peptides were subjected to Edman sequencing and the free phenylthiocarbamyl-labeled amino acids were identified with a Porton 2090 Sequencer (Beckman, Fullerton, Calif.).

Results

Amino Acid Sequencing of Chromatographically-Purified IDBP(s). Two-dimensional PAGE of the [$^3$H]25-OHD3 binding moieties in Peak I from hydroxyapatite chromatography identified at least three distinct proteins in the molecular weight range of interest (60–70 kDa). The dominant, 65 kDa, Coumassie-stained spot displayed a pI of about 4.5. Amino acid composition of the eluted protein(s) revealed the presence of very few cysteine residues, distinguishing this protein(s) from the cysteine-rich proteins in steroid/sterol/thyronine receptor superfamily and in the albumin family of proteins which includes the circulating vitamin D binding protein. Because the amino-terminus of the most abundant protein of interest in the isolate was blocked, the remaining sample was subjected to "in gel" proteolytic digestion prior to amino acid sequence analysis of the proteolytic products. Reverse-phase HPLC of the resultant peptides resulted in the separation and reproducible resolution of seven mass peaks belonging to the parent protein. The amino acid sequence of each was determined after Edman degradation of the peptide fragments. Sequence analysis identified major tryptic peptides ranging in length from 10–15 residues and possessing 89%, 83%, 75%, 70%, 60%, 55%, and 27% amino acid sequence identity to human inducibly expressed hsp70. Two of the three tryptic peptides with most sequence homology to hsp70 were located within the amino-terminal domain of hsp70 (residues 39–128), that region of the hsp70 molecule known to be most conserved among different mammalian species, while the least homologous fragment appeared to reside in the more variable, C-terminal region of hsp70.

EXAMPLE IV
Displacement of Bound Ligant from IDBP By HSP70

If, as the sequence data suggested, IDBP is structurally related to the hsp70 family of proteins and the ligand (sterol) binding domain of IDBP is preserved in hsp70s, then hsp70 should be able to specifically bind [$^3$H]25-OHD3. This experiment was designed to compare the sterol ligand binding activity of hsp70 to that of IDBP.

Materials and Methods

Inducibly-expressed, recombinant human heat shock protein-70 (hsp70) was purchased from StressGen, Victoria, B.C., Canada. Competitive ligand binding experiments were performed as described above. Each data point was the mean of triplicate assessments of total binding; total [$^3$H] 25-hydroxyvitamin D3 binding by hsp70 in the absence of added sterol was the mean±SD of six replicate determinations.

Results

Inducibly-expressed hsp70 exhibited specific [$^3$H]25-OHD3 binding activity. The concentration of radioinert 25-hydroxyvitamin D3 required to achieve maximal displacement of [$^3$H] 25-hydroxyvitamin D3 was approximately the same (50–100 nM) for both IDBP and inducibly expressed hsp70.

EXAMPLE V
Cloning of a cDNA Encoding NWP IDBP

A cDNA library prepared from B95-8 cell RNA was screened by PCR using oligonuleotide primers based upon the information gained from the amino acid sequencing of the tryptic digests of the IDBP isolated from B95-8 cells.

The sequence of the oligonucleotide primers were as follows:

14A 5'ATGAAGGAGACCGCGGAAGC (SEQ ID NO: 4)
14B 5'ATGAAAGAGACGCCCGAGG (SEQ ID NO: 5)
15A 5'GTACCCAGCAGGTGGTTGTC (SEQ ID NO: 6)
15B 5'GTCCCCAGCAGATGGTTATC (SEQ ID NO: 7)
HS2 5'CAGGACGACGTCATGAATCTG (SEQ ID NO: 8)
HS1 5'GACGCGGGGGCCATCGCGGGGCTCAAC (SEQ ID NO: 9)

Primers HS1 and HS2 successfully amplified a cDNA probe of about 630 base pairs. This probe was used to clone the IDBP cDNA (SEQ ID NO: 1) shown in the top line of FIG. 3 from the same B95-8 library using standard colony hybridization procedures. When the polynucleotide encoding NWP IDBP (SEQ ID NO: 1) is compared to that encoding human hsp70 (SEQ ID NO: 2) (bottom line of FIG. 3), a very high degree of homology is seen, especially in the coding region. This result indicates that NWP IDBP is probably the hsp70 homolog in New World primates.

EXAMPLE VI
NWP IDBP is Heat Inducible

This experiment was designed to test whether NWP IDBP is a heat shock protein. The following cell lines were subject to 40° C. for one hour: (1) the New World Primate cell line B95, which exhibits vitamin D resistance; (2) the cell line OMK isolated from a New World Primate gibbon species which does not exhibit vitamin D resistance; (3) MLA, an Old World primate; and (4) human. RNA was isolated from cells heat shocked, and from control cells, and subjected to Northern analysis with a partial IDBP cDNA from a B95-8 cell library as a probe. Although B95 cells were the only cell line to show substantial levels of IDBP prior to heat inducement, both OMK and human cells exhibit detectable basal levels. Regardless, upon heat shock, all of the cell lines tested, including the vitamin D resistant line B95, induced expression of IDBP/hsp70.

EXAMPLE VII
Human HSP70 Binds Steroids

To verify that IDBP is indeed the protein responsible for the vitamin D binding activity exhibited by B95 cells, cDNA encoding IDBP was transfected into mammalian cells which did not exhibit this phenotype. The coding region of IDBP shown in FIG. 3 was cloned into pcDNA3.1 (Invitrogen). Cos-7 and OMK gibbon cells, both of which do not exhibit vitamin D resistance or significant 25-OHD3 binding activity were chosen for transient transfections via lipopection (LipoTAXI, Stratagene, Calif.). Control plasmid was the pcDNA3.1 vector without cloned insert.

Cells transfected with the plasmid expressing the IDBP coding region exhibited significant 25-OHD3 binding activity (approximately 0.8 fmol/µg protein for Cos-7 cells, and approximately 1.0 fmol/µg protein for OMK gibbon cells). In contrast, control cells transfected with expression plasmid without insert exhibited negligible 25-OHD3 binding activity.

This experiment was repeated with expression plasmids which encode different fragments of IDBP. The coding region of the cDNA contains a convenient Eco RI restriction site which divides the region encoding the deduced ATP binding from the deduced peptide binding domain and variable domain. Expression constructs containing either the ATP binding domain, or both the peptide binding domain and variable domain were independently transfected into both COS-7 and OMK gibbon cells. only the cells transfected with the construct encoding the ATP binding domain exhibited enhanced 25-OHD3 binding activity, indicating that this region of the protein is sufficient for steroid binding.

Incorporation by Reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of biochemistry, molecular biology or related fields are intended to be within the scope of the following claims.

TABLE I

Identity, 25-OHD3 binding index, and source of potential IDBP ligands tested

| Compounds | RBI* | Source |
| --- | --- | --- |
| Vitamin D-related | | |
| 7-Dehydrocholesterol | 0 | Sigma Co., USA |
| Vltamin D3 | 0 | Sigma Co., USA |

TABLE I-continued

Identity, 25-OHD3 binding index, and source of potential IDBP ligands tested

| Compounds | RBI* | Source |
|---|---|---|
| Vitamin D2 | 0 | Hoffman-LaRoche, USA |
| Dihydrotachysterol | 0 | Sigma Co., USA |
| 1-OHD3 | 0 | Hoffman-LaRoche, USA |
| 25-OHD3 | 100 | Hoffman-LaRoche, USA |
| 25-OHD2 | 100 | Hoffman-LaRoche, USA |
| 1,25-(OH)2D3 | 33 | Hoffman-LaRoche, USA |
| 1,25-(OH)2D2 | 35 | Hoffman-LaRoche, USA |
| 24,25-(OH)2D3 | 72 | Hoffman-LaRoche, USA |
| 25,26-(OH)2D3 | 70 | Hoffman-LaRoche, USA |
| 1,24,25-(OH)3D3 | 36 | Hoffman-LaRoche, USA |
| Calcipotriol (MC903) | 0 | Leo Pharmaceutical, Denmark |
| EB1089 | 0 | Leo Pharmaceutical, Denmark |
| KH1060 | 0 | Leo Pharmaceutical, Denmark |
| Steroids | | |
| Pregnenolone | 0 | Sigma Co., USA |
| Progesterone | 19 | Sigma Co., USA |
| Hydrocortisone | 0 | Sigma Co., USA |
| Cortisone | 0 | Sigma Co., USA |
| Corticosterone (B) | 0 | Sigma Co., USA |
| Deoxycorticosterone (DOC) | 0 | Sigma Co., USA |
| Aldosterone | 0 | Sigma Co., USA |
| DHEA | 0 | Sigma Co., USA |
| DHEAS | 0 | Sigma Co., USA |
| Dexamethasone | 0 | Sigma Co., USA |
| Androstendione | 0 | Sigma Co., USA |
| Androstendiol | 0 | Sigma Co., USA |
| Testosterone | 30 | Sigma Co., USA |
| 5-Dihydroxytestosterone | 0 | Sigma Co., USA |
| 17β-Estradiol | 33 | Sigma Co., USA |
| Tamoxifen | 0 | Sigma Co., USA |
| RU486 | 0 | Roussel-U.C.L.A.F., France |
| Other | | |
| Cholesterol | 0 | Sigma Co., USA |
| 25-Hydroxycholesterol | 0 | Sigma Co., USA |
| Arachidonic acid | 0 | Biomol, USA |
| PGE2 | 0 | Biomol, USA |
| PGF2alpha | 0 | Biomol, USA |
| All-trans Retinoic acid | 0 | Sigma Co., USA |
| 9-cis Retinoic acid | 0 | Biomol, USA |
| Triiodothyronine | 0 | Sigma Co., USA |

*RBI (Relative Binding Index) is the relative ability of the maximally effective concentration of the compound in question to competitively displace [3H]25-OHD3 from IDBP present in the unfractionated, 100,000 × g supernatant extract of B95-8 cells; of the compounds examined 25-OHD3 was the most effective and assigned a score of 100.

TABLE II

IDBP enrichment by cell fractionation (upper panel) and chemical means (lower panel)

Specific Binding Avtivity

Differential Centrifugation

| Cell Fraction | (nmol 25-OHD3/mg prot) |
|---|---|
| whole cells | 0.017 |
| post 4,000 × g sup | 0.057 |
| post 100,000 × g sup | 0.087 |

Serial Column Chromatography

| Fraction | (fold enrichment) |
|---|---|
| cell extract | 1 |
| post-DEAE | 14 |
| post-phenyl-HIC | 63 |
| post-hydroxylapatite | 17,588 |

What is claimed is:

1. A purified intracellular vitamin D binding proteins CIDBP from a new world primate having specific vitamin D binding activity at least about 17,588-fold greater than cell extract containing endogenous IDBP.

2. The purified IDBP according to claim 1, wherein the primate is *Callithrix jacchus*.

3. A purified IDBP from a new world primate having specific vitamin D binding activity at least about 17,588-fold greater than cell extract containing endogenous IDBP and having the amino acid sequence of SEQ ID NO:3 said derivative having vitamin D binding activity.

4. The purified IDBP of claim 2, wherein said purified IDBP comprises the sequence of SEQ ID NO:3.

5. A functional derivative of a purified IDBP from a new world primate having specific vitamin D binding activity at least about 17,588-fold greater than cell extract containing endogenous IDBP and comprising at least 95% identity to the sequence of SEQ ID NO:3 said derivative having vitamin D binding activity.

6. The functional derivative of claim 5, wherein said functional derivative binds vitamin D and related steroid molecules.

7. A functional fragment of a purified IDBP from a new world primate having specific vitamin D binding activity at least about 17,588-fold greater than cell extract containing endogenous IDBP and having the amino acid sequence of SEO ID NO:3, wherein said fragment has vitamin D binding activity.

8. The functional fragment of claim 7, comprising about amino acid residues 8 to 388 of SEQ ID NO:3.

9. The functional fragment of claim 7, consisting of amino acid residues 8 to 388 of SEQ ID NO:3.

10. The functional fragment of claim 7, comprising about amino acid residues 389 to 547 of SEQ ID NO:3.

11. The functional fragment of claim 7, consisting of amino acid residues 389 to 547 of SEQ ID NO:3.

12. The functional fragment of claim 7, comprising about amino acid residues 548 to 643 of SEQ ID NO:3.

13. The functional fragment of claim 7, consisting of amino acid residues 548 to 643 of SEQ ID NO:3.

14. The functional fragment of claim 7, wherein said functional fragment binds vitamin D and related steroid molecules.

15. A purified fusion protein comprising the functional fragment of claim 7.

16. A purified IDBP, from a new world primate having specific vitamin D binding activity at least about 17,588-fold greater than cell extract containing endogenous IDBP and encoded by the nucleotide sequence of SEQ ID NO:1, or a functional fragment thereof which binds vitamin D.

17. The purified IDBP of claim 16, wherein said IDBP is full-length IDBP.

18. The purified IDBP of claim 16, wherein said functional fragment comprises about amino acid residues 8 to 388 of SEQ ID NO:3.

19. The purified IDBP of claim 16, wherein said functional fragment consists of amino acid residues 8 to 388 of SEQ ID NO:3.

20. The purified IDBP of claim 16, wherein said functional fragment comprises about amino acid residues 389 to 547 of SEQ ID NO:3.

21. The purified IDBP of claim 16, wherein said functional fragment consists of amino acid residues 389 to 547 of SEQ ID NO:3.

22. The purified IDBP of claim 16, wherein said functional fragment comprises about amino acid residues 548 to 643 of SEQ ID NO:3.

23. The purified IDBP of claim 16, wherein said functional fragment consists of amino acid residues 548 to 643 of SEQ ID NO:3.

24. The purified IDBP of claim 16, wherein said functional fragment binds vitamin D and related steroid molecules.

25. A purified fusion protein comprising the purified IDBP of claim 16.

26. A functional fragment of a purified IDBP from a new world primate having specific vitamin D binding activity at least about 17,588-fold greater than cell extract containing endogenous IDBP, wherein said functional fragment contains one or more binding sites for molecules selected from the group of vitamin D and related steroids, peptide substrate, wherein said peptide substrate is that bound by the protein of SEQ ID NO: 3, and ATP.

27. A purified IDBP, or fragment thereof, encoded by the nucleotide sequence of SEQ ID NO:1, wherein said IDBP or fragment contains one or more binding sites for molecules selected from the group of vitamin D and related steroids, peptide substrate wherein said peptide substrate is that bound by the protein of SEQ ID NO: 3 and ATP.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 2394 base pairs
      (B) TYPE: nucleic acid
      (C) STRANDEDNESS: unknown
      (D) TOPOLOGY: unknown (ii) MOLECULE TYPE: cDNA (xi) SEQUENCE DESCRIPTION: SEQ ID NO: 1:

```
GCGGCGCCGT CCCGCTGAGT CAGCCCGGGA GGGCGGGAGG CTCTCTGCCG GCCGGGAAAG      60

TGCGGGAANG TTCGCGGCGG CGCNGGCGGG AAGAAGCGCA ANCGGATAAA AAGCCCGTGG     120

AAGCGAANCG CANTANATCC GARCCGGGCT GGCCGGAAAC AAATCGCGGG GAGACCCACG     180

GCGGAGCGCC CTTCGACTGC TGATCGGCAG CAGCCTCAAC GGCCTCGAGC ATCCACGAWA     240
```

```
AGCTTCAGCC ATGCAGGCCC CACGGGAGCT GGCGGTGGGC ATCGACCTGG GCACCACCTA    300

CTCGTGCGTG GGCGTGTTCA CAACAGGGCC GCGTGGAGAT CCTGGCCAAC GAACNAGGGC    360

AACCGCACCA MGCCMATCTA CGTKGCCTTC ACTGACACCA ACCNGCTGGT CNGGACGCN     420

GCCATCAACC AAGCGGSCCT GAACCCGCTC AACACGGTGT TCNACGCCAA TCGGCGGTGA    480

TCGGGCGCAA GTTCGCGGAC GCCACGGTGC AGGCGGACAT GAAGCACTGG CCCTTCCAGG    540

TGGTGAGCGA GGGCTGCAAG CCCAAGGTGC GCGTGTCCTA CCGCGGGGAG GACAAGTCGT    600

TCTACCCCGA GGAGATCTCG TCCATGGTGC TGAGCAAGAT GAAGGAGACG GCCGAGGCGT    660

ATCTGGGCCA GCCCGTGAAG CACGCTGTGA TCACCGTGCC CGCCTACTTC AATGACTCGC    720

AGCGCCAGGC CACCAAGGAC GCGGGCGCTA TCGCGGGGCT CAACGTGCTG CGGATCATCA    780

ACGAACCTAC GGCTGCCGCC ATCGCCCATG GGCTGGACCG GCGCGGCGCG GGAGAACGCA    840

ACGTGCTCAT TTTTGACCTG GGTGGGGGCA CCTTCGACGT GTCCGTTCTC TCCATTGACG    900

CCGGTGTCTT TGAGGTGAAA GCCACTGCTG GAGACACCCA CTTGGGTGGA GARGACTTCG    960

ACAACCGGTT GGTGAACCAC TTTGTGGAAG AATTCCGGCG GAAGCATCSG AAGGACCTGA   1020

GCTGGAACAA GANGGCCCTT CGCAGGCTGC GCACAGCCTG TGAGCGCGCC AAGCGCACCC   1080

TGTCCTCCAG CACCCAGGCC ACCCTGGANA TTGACTCCCT GTTCGARGGC GTGGACTTCT   1140

ACACGTCCAT CACTCGTGCC CGCTTTGANG AACTGTGCTC ANACCTCTTC CGCANCACTC   1200

TGGAACCGGT ANAAAAAGSC CTGCGGGATG CCAANCTGGA CAAGGCCANA TCCATGACGT   1260

CSTCCTGGGT GGGGGGCTCC ACTCSCATCC CCARGGTACA RAAGTTGCTG CAGGACTTCT   1320

TCMACGGCAA GGAGCTGAAC AAGAGCATCA ACCCTGATGA AGCTGTGGCC TATGGGGCTG   1380

CGGTGCANGC GGCCGTGTTG ATGGGGGACA AGTGTGAGAA AGTGCGGGAT CTTCTGCTGC   1440

TGGATGTGGC TCCCCTGTCT CTAGGGCTGG AGACAGCAGG TGGGGTGATG ACTACGCTTA   1500

TCCAGAGGAA TGCCACTATC CCCACCAAGC AGACCCAGAC TTTCACCACC TACTCGGACA   1560

ACCAGCCTGG GGTCTTCATC CANGTGTATG ANGGTGAGAG GGCCATGACC AANGACAACA   1620

ACCTGCTGGG GCGCTTTGAA CTCAGTGGCA TCCCTCCTGC CCCACGTGGA GTCCCCCAGA   1680

TANAAGTGAC CTTTGACATT GATGCTAATG GCATCCTGAG TGTGACAGCC ACTGACAGGA   1740

GCACAGGTAA GGCTAACAAG ATCACCATCA CCAATGACAA GGGCCGGCTG AGCAAGGAAG   1800

AGGTGGAGAG GATGGTTCGT GAGGCCGANC AATACAAAGC TGAGGATGAG GCCCAGAGGG   1860

ACAGAGTGGC TGCCAAAAAC TCGTTGGAGA CCCATGTCTT CCATGTGAAA GGTTCTTTGC   1920

AAGAGGAAAG CCTTAGGGAC AAGATTCCCA AAGAGGACAG GCACAAAGTG CAAGACAAGT   1980

GTCAGGAAGT CCTTGCCTGG CTGGAGCACA ACCAGCTGGC AGACAAGGAG GAGTATGAGC   2040

ATCAGAAGAR GGAGCTGGAG CAAATCTGTC GCCCCATCTT CTCCAGGCTC TTAWGGGGGA   2100

CCTKGTGTCC CTGGGGGCAG CAGTTGTGGC GYTCAAGCCC GCCAGGGGGA CCGCAGCACC   2160

GGCCCCATCA TTGARGARGT TGATTGAATG GCCCTTTGTG ATAAGTCAGC TGTGACTGTA   2220

AGGGCTATGC TGTKGGCCTT CTAGACTGTT TCTATGATCC TGCCCTTCCG AGATGAAGGG   2280

CTGGGGAATC TTCCCCGCAA AGCTAGAGCT TTCTTCTCAG GATGTTTCAT AACTGAAGTC   2340

TTTTGACTTT TCGGTGAGAG AGAGGTTCAT CCTCTTCTGC TTCAAATTAA AAGT          2394
```

(2) INFORMATION FOR SEQ ID NO: 2:

(i) SEQUENCE CHARACTERISTICS:
        (A) LENGTH: 2379 base pairs
        (B) TYPE: nucleic acid (C) STRANDEDNESS: unknown
(D) TOPOLOGY: unknown (ii) MOLECULE TYPE: cDNA (xi) SEQUENCE DESCRIPTION: SEQ ID NO: 2:

```
CCCGGGCGGG CGAGAGGCTC TCAACTGGGC GGGAAGGTGC GGGAAGGTGC GGAAAGGTTC      60
GCGAAAGTTC GCGGCGGCGG GGGTCGGGTG AGGCGCAAAA GGATAAAAAG CCCGTGGAAG     120
CGGAGCTGAG CAGATCCGAG CCGGGCTGGC TGCAGAGACA CCGCAGGGAG AGCCTCACTG     180
CTGAGCGAAA ATCGACGGCG GACGGGCAGC AGCCTCCGTG GCCTCCAGCA TCCGACAAGA     240
AGCTTCAGCC ATGCAGGCCC ACGGGAGCT CGCGGTGGGC ATCGACCTGG GCACCACCTA      300
CTCGTGCGTG GGCGTGTTTC AGCAGGGCCG CGTGGAGATC CTGGCCAACG ACCAGGGCAA     360
CCGCACCACG CCCAGCTACG TGGCCTTCAC CGACACCGAG CGGCTGGTCG GGACGCGGC      420
CAAGAGCCAG GCGGCCCTGA ACCCCACAA CACCGTGTTC GATGCCAAGC GGCTGATCGG      480
GCGCAAGTTC GCGGACACCA CGGTGCAGTC GGACATGAAG CACTGGCCCT TCCGGGTGGT     540
GAGCGAGGGC GGCAAGCCCA AGGTGCCGGT ATCGTACCGC GGGGAGGACA AGACGTTCTA    600
CCCCGAGGAG ATCTCGTCCA TGGTGCTGAG CAAGATGAAG GAGACGGCCG AGGCGTACCT    660
GGGCCAGCCC GTGAAGCACG CAGTGATCAC CGTGCCCGCC TATTTCAATG ACTCGCAGCG    720
CCAGGCCACC AAGGACGCGG GGGCCATCGC GGGGCTCAAC GTGTTGCGGA TCATCAATGA    780
GCCCACGGCA GCTGCCATCG CCTATGGGCT GGACCGGCGG GGCGCGGGAG AGCGCAACGT    840
GCTCATTTTT GACCTGGGTG GGGCACCTT CGATGTGTCG GTTCTCTCCA TTGACGCTGG     900
TGTCTTTGAG GTGAAAGCCA CTGCTGGAGA TACCCACCTG GGAGGAGAGG ACTTCGACAA    960
CCGGCTCGTG AACCACTTCA TGGAAGAATT CCGGCGGAAG CATGGGAAGG ACCTGAGCGG    1020
GAACAAGCGT GCCCTCGGCA GGCTGCGCAC AGCCTGTGAG CGCGCCAAGC GCACCCTGTC    1080
CTCCAGCACC CAGGCCACCC TGGAGATAGA CTCCCTGTTC GAGGGCGTGG ACTTCTACAC    1140
GTCCATCACT CGTGCCCGCT TTGAGGAACT GTGCTCAGAC CTCTTCCGCA GCACCCTGGA    1200
GCCGGTGGAG AAGGCCCTGC GGGATGCCAA GCTGGACAAG GCCCAGATTC ATGACGTCGT    1260
CCTGGTGGGG GGCTCCACTC GCATCCCCAA GGTGCAGAAG TTGCTGCAGG ACTTCTTCAA    1320
CGGCAAGGAG CTGAACAAGA GCATCAACCC TGATGAGGCT GTGGCCTATG GGCTGCTGT     1380
GCAGGCGGCC GTGTTGATGG GGGACAAATG TGAGAAAGTG CAGGATCTCC TGCTGCTGGA    1440
TGTGGCTCCC CTGTCTCTGG GGCTGGAGAC AGCAGGTGGG GTGATGACCA CGCTGATCCA    1500
GAGGAACGCC ACTATCCCCA CCAAGCAGAC CCAGACTTTC ACCACCTACT CGGACAACCA    1560
GCCTGGGGTC TTCATCCAGG TGTATGAGGG TGAGAGGGCC ATGACCAAGG ACAACAACCT    1620
GCTGGGGCGT TTTGAACTCA GTGGCATCCC TCCTGCCCCA CGTGGAGTCC CCCAGATAGA    1680
GGTGACCTTT GACATTGATG CTAATGGCAT CCTGAGCGTG ACAGCCACTG ACAGGAGCAC    1740
AGGTAAGGCT AACAAGATCA CCATCACCAA TGACAAGGGC CGGCTGAGCA AGGAGGAGGT    1800
GGAGAGGATG GTTCATGAAG CCGAGCAGTA CAAGGCTGAG GATGAGGCCC AGAGGGACAG    1860
AGTGGCTGCC AAAAACTCGC TGGAGGCCCA TGTCTTCCAT GTGAAAGGTT CTTTGCAAGA    1920
GGAAAGCCTT AGGGACAAGA TTCCCGAAGA GGACAGGCGC AAAATGCAAG ACAAGTGTCG    1980
GGAAGTCCTT GCCTGGCTGG AGCACAACCA GCTGGCAGAG AAGGAGGAGT ATGAGCATCA    2040
GAAGAGGGAG CTGGAGCAAA TCTGTCGCCC CATCTTCTCC AGGCTCTATG GGGGCCTGG     2100
TGTCCCTGGG GGCAGCAGTT GTGGCACTCA AGCCCGCCAG GGGGACCCCA GCACCGGCCC    2160
```

```
CATCATTGAG GAGGTTGATT GAATGGCCCT TCGTGATAAG TCAGCTGTGA CTGTCAGGGC    2220

TATGCTATGG GCCTTCTAGA CTGTCTTCTA TGATCCTGCC CTTCAGAGAT GAACTTTCCC    2280

TCCAAAGCTA GAACTTTCTT CCCAGGATAA CTGAAGTCTT TTGACTTTTT GCGGGGAGGG    2340

CGGTTCATCC TCTTCTGCTT CAAATAAAAA GTCATTAAT                           2379
```

(2) INFORMATION FOR SEQ ID NO: 3:

(i) SEQUENCE CHARACTERISTICS:
        (A) LENGTH: 643 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 3:

```
Met Gln Ala Pro Arg Glu Leu Ala Val Gly Ile Asp Leu Gly Thr Thr
1               5                   10                  15

Tyr Ser Cys Val Gly Val Phe Gln Gln Gly Arg Val Glu Ile Leu Ala
            20                  25                  30

Asn Asp Gln Gly Asn Arg Thr Thr Pro Ile Tyr Val Ala Phe Thr Asn
        35                  40                  45

Thr Asn Arg Leu Val Gly Asp Ala Ala Ile Asn Gln Ala Ala Leu Asn
    50                  55                  60

Pro Leu Asn Thr Val Phe Asp Ala Asn Arg Leu Ile Gly Arg Lys Phe
65                  70                  75                  80

Ala Asp Ala Thr Val Gln Ala Asp Met Lys His Trp Pro Phe Gln Val
                85                  90                  95

Val Ser Glu Gly Cys Lys Pro Lys Val Arg Val Ser Tyr Arg Gly Glu
            100                 105                 110

Asp Lys Ser Phe Tyr Pro Glu Glu Ile Ser Ser Met Val Leu Ser Lys
        115                 120                 125

Met Lys Glu Thr Ala Glu Ala Tyr Leu Gly Gln Pro Val Lys His Ala
    130                 135                 140

Val Ile Thr Val Pro Ala Tyr Phe Asn Asp Ser Gln Arg Gln Ala Thr
145                 150                 155                 160

Lys Asp Ala Gly Ala Ile Val Gly Leu Asn Val Leu Arg Ile Ile Asn
                165                 170                 175

Glu Pro Thr Ala Ala Ala Ile Ala His Gly Leu Asp Arg Arg Gly Ala
            180                 185                 190

Gly Glu Arg Asn Val Leu Ile Phe Asp Leu Gly Gly Gly Thr Phe Asn
        195                 200                 205

Val Ser Val Leu Ser Ile Asp Ala Gly Val Phe Glu Val Lys Ala Thr
    210                 215                 220

Ala Gly Asp Thr His Leu Gly Gly Glu Asp Phe Asp Asn Arg Leu Val
225                 230                 235                 240

Asn His Phe Val Glu Glu Phe Arg Arg Lys His Arg Lys Asp Leu Ser
                245                 250                 255

Trp Asn Lys Arg Ala Leu Arg Arg Leu Arg Thr Ala Cys Glu Arg Ala
            260                 265                 270

Lys Arg Thr Leu Ser Ser Ser Thr Gln Ala Thr Leu Glu Ile Asp Ser
        275                 280                 285

Leu Phe Glu Gly Val Asp Phe Tyr Thr Ser Ile Thr Arg Ala Arg Phe
    290                 295                 300

Glu Glu Leu Cys Ser Asp Leu Phe Arg Ser Thr Leu Glu Pro Val Glu
```

```
305                 310                 315                 320

Lys Gly Leu Arg Asp Ala Lys Leu Asp Lys Ala Xaa Ile His Asp Val
                325                 330                 335

Val Leu Val Gly Gly Ser Thr Arg Ile Pro Arg Val Gln Lys Leu Leu
                340                 345                 350

Gln Asp Phe Phe Asn Gly Lys Glu Leu Asn Lys Ser Ile Asn Pro Asn
                355                 360                 365

Glu Ala Val Ala Tyr Gly Ala Ala Val Gln Ala Ala Val Leu Met Gly
                370                 375                 380

Asp Lys Cys Glu Lys Val Arg Asp Leu Leu Leu Leu Asp Val Ala Pro
385                 390                 395                 400

Leu Ser Leu Gly Leu Glu Thr Ala Gly Gly Val Met Thr Thr Leu Ile
                405                 410                 415

Gln Arg Asn Ala Thr Ile Pro Thr Lys Gln Thr Gln Thr Phe Thr Thr
                420                 425                 430

Tyr Ser Asp Asn Gln Pro Gly Val Phe Ile Gln Val Tyr Glu Gly Glu
                435                 440                 445

Arg Ala Met Thr Lys Asp Asn Asn Leu Leu Gly Arg Phe Glu Leu Ser
                450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Ser Val Thr Ala Thr Asp Arg Ser
                485                 490                 495

Thr Gly Lys Ala Asn Lys Ile Thr Ile Thr Asn Asp Lys Gly Arg Leu
                500                 505                 510

Ser Lys Glu Glu Val Glu Arg Met Val Arg Glu Ala Glu Gln Tyr Lys
                515                 520                 525

Ala Glu Asp Glu Ala Gln Arg Asp Arg Val Ala Ala Lys Asn Ser Leu
                530                 535                 540

Glu Thr His Val Phe His Val Lys Gly Ser Leu Gln Glu Glu Ser Leu
545                 550                 555                 560

Arg Asp Lys Ile Pro Lys Glu Asp Arg His Lys Val Gln Asp Lys Cys
                565                 570                 575

Gln Glu Val Leu Ala Trp Leu Glu His Asn Gln Leu Ala Asp Lys Glu
                580                 585                 590

Glu Tyr Glu His Gln Lys Arg Glu Leu Glu Gln Ile Cys Arg Pro Ile
                595                 600                 605

Phe Ser Arg Leu Tyr Gly Gly Phe Gly Val Pro Gly Gly Ser Ser Cys
                610                 615                 620

Gly Ala Gln Ala Arg Gln Gly Asp Arg Ser Thr Gly Pro Ile Ile Glu
625                 630                 635                 640

Glu Val Asp (2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 4:

ATGAAGGAGA CCGCGGAAGC                                            20
```

(2) INFORMATION FOR SEQ ID NO: 5:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 5:

ATGAAAGAGA CGCCCGAGG                                                    19

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 6:

GTACCCAGCA GGTGGTTGTC                                                   20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 7:

GTCCCCAGCA GATGGTTATC                                                   20

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 8:

CAGGACGACG TCATGAATCT G                                                 21

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 9:

GACGCGGGGG CCATCGCGGG GCTCAAC                                           27